(12) United States Patent
Coe et al.

(10) Patent No.: US 8,142,452 B2
(45) Date of Patent: Mar. 27, 2012

(54) CONTROLLING PRESSURE IN ADJUSTABLE RESTRICTION DEVICES

(75) Inventors: Jonathan A. Coe, Cincinnati, OH (US); Christopher W. Widenhouse, Clarksville, OH (US); Thomas E. Adams, Maineville, OH (US); Juan S. Ezolino, Weston, FL (US); David Martin, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 975 days.

(21) Appl. No.: 11/965,331

(22) Filed: Dec. 27, 2007

(65) Prior Publication Data
US 2009/0171375 A1   Jul. 2, 2009

(51) Int. Cl.
*A61B 17/12* (2006.01)
*F04B 23/04* (2006.01)

(52) U.S. Cl. ........... 606/151; 600/37; 417/203; 417/205

(58) Field of Classification Search ................ 606/151; 600/37, 29–31; 604/141–144; 607/35; 417/203, 417/205
See application file for complete search history.

(56) References Cited

U.S. PATENT DOCUMENTS

| | | |
|---|---|---|
| RE3,036 E | 7/1868 | Shunk |
| RE3,037 E | 7/1868 | Tucker |
| RE3,115 E | 9/1868 | Lewis |
| RE3,187 E | 11/1868 | Winchester |
| RE3,322 E | 3/1869 | Murch |
| 236,373 A | 1/1881 | Spilman |
| 322,388 A | 7/1885 | Lord |
| 400,401 A | 3/1889 | Gutzkow |
| D23,637 S | 9/1894 | Casad et al. |
| D24,900 S | 11/1895 | Clemecet |
| D25,318 S | 3/1896 | Perky |
| D27,151 S | 6/1897 | Moulten |
| D29,715 S | 11/1898 | Wheeler |
| D29,745 S | 11/1898 | Bunker |
| D29,885 S | 12/1898 | Gillespie et al. |
| D30,690 S | 5/1899 | Schwedtmann |
| D30,966 S | 6/1899 | Howe |
| D31,230 S | 7/1899 | Hogan |
| 689,758 A | 12/1901 | Shaw |
| 724,913 A | 4/1903 | Montgomery |
| 899,477 A | 9/1908 | Williams |

(Continued)

FOREIGN PATENT DOCUMENTS

CA   1059035   7/1979

(Continued)

OTHER PUBLICATIONS

European Search Report, Application No. 08254160.8, Issued May 8, 2009, 7 pages.

(Continued)

*Primary Examiner* — Julian Woo
*Assistant Examiner* — Christopher L Templeton
(74) *Attorney, Agent, or Firm* — Nutter McClennen & Fish LLP

(57) ABSTRACT

Methods and devices are provided for regulating a hydraulic restriction system including a restriction device. In general, the methods and devices can allow for non-invasive, transient pressure control. The methods and devices can also, in some embodiments, mechanically regulate pressure of the restriction device without using any electrical components that may need to be powered to operate over extended periods of time.

16 Claims, 9 Drawing Sheets

U.S. PATENT DOCUMENTS

| | | |
|---|---|---|
| 926,197 A | 6/1909 | Kim |
| 953,875 A | 4/1910 | Waring |
| 991,192 A | 5/1911 | Batttenfeld |
| 1,087,988 A | 2/1914 | Sheldon |
| 1,210,701 A | 1/1917 | Ryden |
| 1,219,296 A | 3/1917 | Hahn |
| 1,224,355 A | 5/1917 | Brown |
| 1,263,914 A | 4/1918 | Martin |
| 1,310,290 A | 7/1919 | Piechowicz |
| 1,384,873 A | 7/1921 | Strickland |
| 1,421,507 A | 7/1922 | Lindberg |
| 1,551,525 A | 8/1925 | Hamer |
| 1,560,973 A | 11/1925 | Cheron |
| 1,620,633 A | 3/1927 | Colvin |
| 1,623,403 A | 4/1927 | Friel |
| 1,689,085 A | 10/1928 | Russell et al. |
| 1,764,071 A | 6/1930 | Foulke |
| 1,782,704 A | 11/1930 | Woodruff |
| 1,807,107 A | 5/1931 | Sternberch |
| 1,865,446 A | 7/1932 | Sears |
| 1,882,338 A | 10/1932 | Reed et al. |
| 1,924,781 A | 8/1933 | Gaiser |
| 2,027,875 A | 1/1936 | Odend'hal |
| 2,063,430 A | 12/1936 | Graser |
| 2,099,160 A | 11/1937 | Charch |
| 2,105,127 A | 1/1938 | Petrone |
| 2,106,192 A | 1/1938 | Saville |
| 2,143,429 A | 1/1939 | Auble |
| 2,166,603 A | 7/1939 | Menzer |
| 2,168,427 A | 8/1939 | McConkey |
| 2,174,525 A | 10/1939 | Padernal |
| 2,177,564 A | 10/1939 | Havill |
| 2,178,463 A | 10/1939 | Bahnson |
| 2,180,599 A | 11/1939 | Menasco |
| 2,203,460 A | 6/1940 | Fieber |
| 2,206,038 A | 7/1940 | Ford |
| 2,216,374 A | 10/1940 | Martin |
| 2,223,699 A | 12/1940 | Norgren |
| 2,225,145 A | 12/1940 | Baumbach |
| 2,225,880 A | 12/1940 | Montelius |
| 2,261,060 A | 10/1941 | Giesler |
| 2,261,355 A | 11/1941 | Flynn |
| 2,295,539 A | 9/1942 | Beach |
| 2,303,108 A | 11/1942 | Blackburn |
| 2,303,502 A | 12/1942 | Rous |
| 2,318,819 A | 5/1943 | Verson |
| 2,327,407 A | 8/1943 | Edyvean |
| 2,327,615 A | 8/1943 | Ankarlo |
| 2,354,571 A | 7/1944 | Blain |
| 2,426,392 A | 8/1947 | Fennema |
| 2,426,817 A | 9/1947 | Charlton et al. |
| 2,440,260 A | 4/1948 | Gall |
| 2,442,573 A | 6/1948 | Stafford |
| 2,453,217 A | 11/1948 | Gregg et al. |
| 2,455,859 A | 12/1948 | Foley |
| 2,477,922 A | 8/1949 | Emery et al. |
| 2,478,876 A | 8/1949 | Nelson |
| 2,482,392 A | 9/1949 | Whitaker |
| 2,494,881 A | 1/1950 | Kost |
| 2,509,210 A | 5/1950 | Clark |
| 2,509,673 A | 5/1950 | Church |
| 2,511,765 A | 6/1950 | Bradbury |
| 2,520,056 A | 8/1950 | Pozun |
| 2,521,976 A | 9/1950 | Hays |
| 2,533,924 A | 12/1950 | Foley |
| 2,538,259 A | 1/1951 | Merriman |
| 2,581,479 A | 1/1952 | Grashman |
| 2,600,324 A | 6/1952 | Rappaport |
| 2,606,003 A | 8/1952 | McNeill |
| 2,615,940 A | 10/1952 | Williams |
| 2,632,447 A | 3/1953 | Dobes |
| 2,639,342 A | 5/1953 | Cope |
| 2,640,119 A | 5/1953 | Bradford, Jr. |
| 2,641,742 A | 6/1953 | Wolfe |
| 2,651,304 A | 9/1953 | Browner |
| 2,665,577 A | 1/1954 | Sanowskis |
| 2,673,999 A | 4/1954 | Shey |
| 2,676,609 A | 4/1954 | Pfarrer |
| 2,684,118 A | 7/1954 | Osmun |
| 2,689,611 A | 9/1954 | Martinson |
| 2,697,435 A | 12/1954 | Ray |
| 2,723,323 A | 11/1955 | Niemi |
| 2,734,992 A | 2/1956 | Elliot et al. |
| 2,740,007 A | 3/1956 | Amelang |
| 2,740,853 A | 4/1956 | Hatman, Jr. |
| 2,742,323 A | 4/1956 | Shey |
| 2,747,332 A | 5/1956 | Morehouse |
| 2,753,876 A | 7/1956 | Kurt |
| 2,756,883 A | 7/1956 | Schreck |
| 2,756,983 A | 7/1956 | Furcini |
| 2,761,603 A | 9/1956 | Fairchild |
| 2,773,312 A | 12/1956 | Peck |
| 2,783,728 A | 3/1957 | Hoffmann |
| 2,787,875 A | 4/1957 | Johnson |
| 2,793,379 A | 5/1957 | Moore |
| 2,795,460 A | 6/1957 | Bletcher |
| 2,804,514 A | 8/1957 | Peters |
| 2,822,113 A | 2/1958 | Joiner, Jr. |
| 2,831,478 A | 4/1958 | Uddenberg et al. |
| 2,864,393 A | 12/1958 | Drake |
| 2,865,541 A | 12/1958 | Hicks |
| 2,870,024 A | 1/1959 | Martin |
| 2,883,995 A | 4/1959 | Bialous et al. |
| 2,886,355 A | 5/1959 | Wurzel |
| 2,895,215 A | 7/1959 | Neher et al. |
| 2,899,493 A | 8/1959 | Levine |
| 2,902,861 A | 9/1959 | Frost et al. |
| 2,923,531 A | 2/1960 | Bauer et al. |
| 2,924,263 A | 2/1960 | Landis |
| 2,924,432 A | 2/1960 | Arps et al. |
| 2,930,170 A | 3/1960 | Holsman et al. |
| 2,938,592 A | 5/1960 | Charske et al. |
| 2,941,338 A | 6/1960 | Santschi |
| 2,943,682 A | 7/1960 | Ingram, Jr. et al. |
| 2,958,781 A | 11/1960 | Marchal et al. |
| 2,961,479 A | 11/1960 | Bertling |
| 2,976,355 A | 3/1961 | Levine |
| 2,976,686 A | 3/1961 | Stelzer |
| 2,977,876 A | 4/1961 | Meyers |
| 2,986,715 A | 5/1961 | Church et al. |
| 2,989,019 A | 6/1961 | Van Sciver, II |
| 3,010,692 A | 11/1961 | Jentoft |
| 3,013,234 A | 12/1961 | Bourns |
| 3,018,791 A | 1/1962 | Knox |
| 3,034,356 A | 5/1962 | Bieganski |
| 3,040,800 A | 6/1962 | Hartley |
| 3,054,618 A | 9/1962 | Abrams et al. |
| 3,060,262 A | 10/1962 | Hoer |
| 3,070,373 A | 12/1962 | Mathews et al. |
| 3,082,414 A | 3/1963 | Papaminas |
| 3,085,577 A | 4/1963 | Berman et al. |
| 3,096,410 A | 7/1963 | Anderson |
| 3,099,262 A | 7/1963 | Bigliano |
| 3,125,028 A | 3/1964 | Rohde |
| 3,126,029 A | 3/1964 | Englesson |
| 3,129,072 A | 4/1964 | Cook et al. |
| 3,135,914 A | 6/1964 | Callan et al. |
| 3,144,017 A | 8/1964 | Muth |
| 3,151,258 A | 9/1964 | Sonderegger et al. |
| 3,153,460 A | 10/1964 | Raskin |
| 3,161,051 A | 12/1964 | Perry, Jr. |
| 3,167,044 A | 1/1965 | Henrickson |
| 3,171,549 A | 3/1965 | Orloff |
| 3,172,700 A | 3/1965 | Haas |
| 3,173,269 A | 3/1965 | Imbertson |
| 3,182,494 A | 5/1965 | Beatty et al. |
| 3,187,181 A | 6/1965 | Keller |
| 3,187,745 A | 6/1965 | Baum et al. |
| 3,190,388 A | 6/1965 | Moser et al. |
| 3,205,547 A | 9/1965 | Riekse |
| 3,208,255 A | 9/1965 | Burk |
| 3,209,570 A | 10/1965 | Hills |
| 3,221,468 A | 12/1965 | Casey |
| 3,228,703 A | 1/1966 | Wilson |
| 3,229,684 A | 1/1966 | Nagumo et al. |
| 3,236,088 A | 2/1966 | Moller |
| 3,238,624 A | 3/1966 | McCabe |

| | | | | | | |
|---|---|---|---|---|---|---|
| 3,240,510 A | 3/1966 | Spouge | | 3,514,919 A | 6/1970 | Ashton et al. |
| 3,245,642 A | 4/1966 | Dicke | | 3,516,220 A | 6/1970 | Buford et al. |
| 3,255,568 A | 6/1966 | Martin et al. | | 3,517,553 A | 6/1970 | Williams et al. |
| 3,260,091 A | 7/1966 | Shaw, Jr. | | 3,527,226 A | 9/1970 | Hakin et al. |
| 3,265,822 A | 8/1966 | Moulten | | 3,529,908 A | 9/1970 | Smith |
| 3,266,487 A | 8/1966 | Watkins et al. | | 3,530,449 A | 9/1970 | Anderson |
| 3,273,447 A | 9/1966 | Frank | | 3,533,403 A | 10/1970 | Woodson |
| 3,283,352 A | 11/1966 | Hu | | 3,534,728 A | 10/1970 | Barrows |
| 3,290,919 A | 12/1966 | Malinak et al. | | 3,534,872 A | 10/1970 | Roth et al. |
| 3,292,493 A | 12/1966 | Franklin | | 3,535,914 A | 10/1970 | Veith et al. |
| 3,292,888 A | 12/1966 | Fischer | | 3,539,009 A | 11/1970 | Kudlaty |
| 3,294,988 A | 12/1966 | Packard | | 3,543,744 A | 12/1970 | LePar |
| 3,299,603 A | 1/1967 | Shaw | | 3,545,275 A | 12/1970 | Harrison et al. |
| 3,299,882 A | 1/1967 | Masino | | 3,550,583 A | 12/1970 | Chiku |
| 3,301,514 A | 1/1967 | Sugaya | | 3,550,847 A | 12/1970 | Scott |
| 3,302,457 A | 2/1967 | Mayes | | 3,563,094 A | 2/1971 | Rieschel |
| 3,306,384 A | 2/1967 | Ross | | 3,563,245 A | 2/1971 | McLean et al. |
| 3,313,314 A | 4/1967 | Burke et al. | | 3,566,083 A | 2/1971 | McMillin |
| 3,316,935 A | 5/1967 | Kaiser et al. | | 3,566,875 A | 3/1971 | Stoehr |
| 3,320,750 A | 5/1967 | Haise et al. | | 3,568,367 A | 3/1971 | Myers |
| 3,321,035 A | 5/1967 | Tarpley | | 3,568,636 A | 3/1971 | Lockwood |
| 3,332,788 A | 7/1967 | Barnby | | 3,576,554 A | 4/1971 | Temps, Jr. et al. |
| 3,334,510 A | 8/1967 | Hallesy | | 3,580,082 A | 5/1971 | Strack |
| 3,339,401 A | 9/1967 | Peters | | 3,581,402 A | 6/1971 | London et al. |
| 3,340,868 A | 9/1967 | Darling | | 3,583,387 A | 6/1971 | Garner et al. |
| 3,347,162 A | 10/1967 | Braznell | | 3,587,204 A | 6/1971 | George |
| 3,350,944 A | 11/1967 | De Michele | | 3,590,809 A | 7/1971 | London |
| 3,353,364 A | 11/1967 | Blanding et al. | | 3,590,818 A | 7/1971 | Lemole |
| 3,353,481 A | 11/1967 | Antonucci | | 3,590,992 A | 7/1971 | Soderstrom et al. |
| 3,356,334 A | 12/1967 | Scaramucci | | 3,592,183 A | 7/1971 | Watkins et al. |
| 3,356,510 A | 12/1967 | Barnby | | 3,594,519 A | 7/1971 | Schmidlin |
| 3,357,218 A | 12/1967 | Mitchell | | 3,602,885 A | 8/1971 | Grajeda |
| 3,357,461 A | 12/1967 | Friendship | | 3,610,016 A | 10/1971 | Bultman |
| 3,359,741 A | 12/1967 | Nelson | | 3,610,851 A | 10/1971 | Krupski |
| 3,361,300 A | 1/1968 | Kaplan | | 3,611,811 A | 10/1971 | Lissau |
| 3,364,929 A | 1/1968 | Ide et al. | | 3,614,926 A | 10/1971 | Brechtel |
| 3,365,684 A | 1/1968 | Stemke | | 3,614,955 A | 10/1971 | Mirowski et al. |
| 3,378,456 A | 4/1968 | Roberts | | 3,619,742 A | 11/1971 | Rud, Jr. |
| 3,380,445 A | 4/1968 | Frasier | | 3,623,371 A | 11/1971 | Jullien-Davin |
| 3,380,649 A | 4/1968 | Roberts | | 3,624,854 A | 12/1971 | Strong |
| 3,385,022 A | 5/1968 | Anderson | | 3,630,242 A | 12/1971 | Schieser et al. |
| 3,389,355 A | 6/1968 | Schroeder, Jr. | | 3,631,847 A | 1/1972 | Hobbs, II |
| 3,393,612 A | 7/1968 | Gorgens et al. | | 3,633,881 A | 1/1972 | Yurdin |
| 3,396,561 A | 8/1968 | Day | | 3,635,061 A | 1/1972 | Rydell et al. |
| 3,399,667 A | 9/1968 | Nishimoto et al. | | 3,635,074 A | 1/1972 | Moos et al. |
| 3,400,734 A | 9/1968 | Rosenberg | | 3,638,496 A | 2/1972 | King |
| 3,403,237 A | 9/1968 | Wysong | | 3,644,883 A | 2/1972 | Borman et al. |
| 3,409,924 A | 11/1968 | Slama | | 3,648,687 A | 3/1972 | Ramsey, III |
| 3,411,347 A | 11/1968 | Wirth et al. | | 3,651,289 A | 3/1972 | Nagashima et al. |
| 3,417,476 A | 12/1968 | Martens | | 3,651,405 A | 3/1972 | Whitney et al. |
| 3,420,325 A | 1/1969 | McAlister et al. | | 3,653,671 A | 4/1972 | Shipes |
| 3,422,324 A | 1/1969 | Webb | | 3,659,615 A | 5/1972 | Enger |
| 3,426,165 A | 2/1969 | Beaman | | 3,677,685 A | 7/1972 | Aoki et al. |
| 3,438,391 A | 4/1969 | Yocum | | 3,686,958 A | 8/1972 | Porter et al. |
| 3,443,608 A | 5/1969 | Copping et al. | | 3,688,568 A | 9/1972 | Karper et al. |
| 3,445,335 A | 5/1969 | Gluntz | | 3,701,392 A | 10/1972 | Wirth et al. |
| 3,447,281 A | 6/1969 | Bufford et al. | | 3,702,677 A | 11/1972 | Heffington |
| 3,450,153 A | 6/1969 | Hildebrandt et al. | | 3,703,099 A | 11/1972 | Rouse et al. |
| 3,453,546 A | 7/1969 | Fryer | | 3,712,138 A | 1/1973 | Alinari et al. |
| 3,453,848 A | 7/1969 | Williamson | | 3,713,124 A | 1/1973 | Durland et al. |
| 3,456,134 A | 7/1969 | Ko | | 3,719,524 A | 3/1973 | Ripley et al. |
| 3,457,909 A | 7/1969 | Laird | | 3,721,412 A | 3/1973 | Kindorf |
| 3,460,557 A | 8/1969 | Gallant | | 3,723,247 A | 3/1973 | Leine et al. |
| 3,463,338 A | 8/1969 | Schneider | | 3,724,000 A | 4/1973 | Eakman |
| 3,469,818 A | 9/1969 | Cowan | | 3,727,463 A | 4/1973 | Intraub |
| 3,470,725 A | 10/1969 | Brown et al. | | 3,727,616 A | 4/1973 | Lenzkes |
| 3,472,230 A | 10/1969 | Fogarty | | 3,730,174 A | 5/1973 | Madison |
| 3,478,344 A | 11/1969 | Schwitzgebel et al. | | 3,730,560 A | 5/1973 | Abildgaard et al. |
| 3,482,449 A | 12/1969 | Werner | | 3,731,679 A | 5/1973 | Wilhelmson et al. |
| 3,482,816 A | 12/1969 | Arnold | | 3,731,681 A | 5/1973 | Blackshear et al. |
| 3,487,959 A | 1/1970 | Pearne et al. | | 3,732,731 A | 5/1973 | Fussell, Jr. |
| 3,491,842 A | 1/1970 | Delacour et al. | | 3,735,040 A | 5/1973 | Punt et al. |
| 3,492,638 A | 1/1970 | Lane | | 3,736,930 A | 6/1973 | Georgi |
| 3,502,829 A | 3/1970 | Reynolds | | 3,738,356 A | 6/1973 | Workman |
| 3,503,116 A | 3/1970 | Strack | | 3,740,921 A | 6/1973 | Meyer et al. |
| 3,504,664 A | 4/1970 | Haddad | | 3,746,111 A | 7/1973 | Berthiaume et al. |
| 3,505,808 A | 4/1970 | Eschle | | 3,748,678 A | 7/1973 | Ballou |
| 3,509,754 A | 5/1970 | Massingill et al. | | 3,749,098 A | 7/1973 | De Bennetot et al. |
| 3,512,517 A | 5/1970 | Kadish et al. | | 3,749,422 A | 7/1973 | Abildgaard et al. |

| | | | | | |
|---|---|---|---|---|---|
| 3,749,423 A | 7/1973 | Abildgaard et al. | 3,924,635 A | 12/1975 | Hakim et al. |
| 3,750,194 A | 8/1973 | Summers | 3,928,980 A | 12/1975 | Ganzinotti et al. |
| 3,757,770 A | 9/1973 | Brayshaw et al. | 3,929,175 A | 12/1975 | Coone |
| 3,759,095 A | 9/1973 | Short, Jr. et al. | 3,930,682 A | 1/1976 | Booth |
| 3,760,638 A | 9/1973 | Lawson et al. | 3,930,852 A | 1/1976 | Tanaka et al. |
| 3,763,960 A | 10/1973 | John et al. | 3,936,028 A | 2/1976 | Norton et al. |
| 3,765,142 A | 10/1973 | Lindquist et al. | 3,940,122 A | 2/1976 | Janzen et al. |
| 3,765,494 A | 10/1973 | Kielman, Jr. | 3,940,630 A | 2/1976 | Bergonz |
| 3,769,156 A | 10/1973 | Brecy et al. | 3,942,299 A | 3/1976 | Bory et al. |
| 3,769,830 A | 11/1973 | Porter et al. | 3,942,382 A | 3/1976 | Hok et al. |
| 3,774,243 A | 11/1973 | Ng et al. | 3,942,516 A | 3/1976 | Glynn et al. |
| 3,776,333 A | 12/1973 | Mathauser | 3,942,536 A | 3/1976 | Mirowski et al. |
| 3,778,051 A | 12/1973 | Allen et al. | 3,943,915 A | 3/1976 | Severson |
| 3,780,578 A | 12/1973 | Sellman et al. | 3,945,704 A | 3/1976 | Kraus et al. |
| 3,781,902 A | 12/1973 | Shim et al. | 3,946,613 A | 3/1976 | Silver |
| 3,783,585 A | 1/1974 | Hoyland et al. | 3,946,615 A | 3/1976 | Hluchan |
| 3,789,667 A | 2/1974 | Porter et al. | 3,946,724 A | 3/1976 | La Balme et al. |
| 3,796,095 A | 3/1974 | Fussell, Jr. | 3,948,141 A | 4/1976 | Shinjo et al. |
| 3,807,219 A | 4/1974 | Wallskog | 3,949,388 A | 4/1976 | Fuller |
| 3,811,429 A | 5/1974 | Fletcher et al. | 3,953,289 A | 4/1976 | Costes et al. |
| 3,815,722 A | 6/1974 | Sessoms | 3,954,271 A | 5/1976 | Tredway, Sr. |
| 3,818,765 A | 6/1974 | Eriksen et al. | 3,958,558 A | 5/1976 | Dunphy et al. |
| 3,820,400 A | 6/1974 | Russo | 3,961,425 A | 6/1976 | Swanson et al. |
| 3,820,795 A | 6/1974 | Taylor | 3,961,646 A | 6/1976 | Schon et al. |
| 3,823,610 A | 7/1974 | Fussell, Jr. | 3,962,895 A | 6/1976 | Rydell et al. |
| 3,825,065 A | 7/1974 | Lloyd et al. | 3,962,921 A | 6/1976 | Lips |
| 3,825,963 A | 7/1974 | Abildgaard et al. | 3,963,019 A | 6/1976 | Quandt |
| 3,825,964 A | 7/1974 | Groswith, III et al. | 3,964,485 A | 6/1976 | Neumeier |
| 3,828,672 A | 8/1974 | Gazzola et al. | 3,964,770 A | 6/1976 | Abildgaard et al. |
| 3,828,766 A | 8/1974 | Krasnow | 3,967,737 A | 7/1976 | Peralta et al. |
| 3,831,588 A | 8/1974 | Rindner | 3,968,473 A | 7/1976 | Patton et al. |
| 3,831,942 A | 8/1974 | Del Mar | 3,968,694 A | 7/1976 | Clark |
| 3,833,238 A | 9/1974 | Liard et al. | 3,972,320 A | 8/1976 | Kalman |
| 3,834,167 A | 9/1974 | Tabor | 3,973,753 A | 8/1976 | Wheeler |
| 3,834,739 A | 9/1974 | Abildgaard et al. | 3,973,858 A | 8/1976 | Poisson et al. |
| 3,835,523 A | 9/1974 | Stansfield et al. | 3,974,655 A | 8/1976 | Halpern et al. |
| 3,839,708 A | 10/1974 | Bredesen et al. | 3,974,865 A | 8/1976 | Fenton et al. |
| 3,842,483 A | 10/1974 | Cramer | 3,977,391 A | 8/1976 | Fleischmann |
| 3,842,668 A | 10/1974 | Lippke et al. | 3,980,871 A | 9/1976 | Lindstrom et al. |
| 3,845,664 A | 11/1974 | Perry, Jr. | 3,982,571 A | 9/1976 | Fenton et al. |
| 3,845,751 A | 11/1974 | Runstetler | 3,983,948 A | 10/1976 | Jeter |
| 3,845,757 A | 11/1974 | Weyer | 3,985,133 A | 10/1976 | Jenkins et al. |
| 3,847,434 A | 11/1974 | Weman et al. | 3,987,860 A | 10/1976 | Jabsen |
| 3,850,208 A | 11/1974 | Hamilton | 3,989,005 A | 11/1976 | Bowler, Jr. et al. |
| 3,853,117 A | 12/1974 | Murr | 3,991,749 A | 11/1976 | Zent |
| 3,854,469 A | 12/1974 | Giori et al. | 3,992,948 A | 11/1976 | D'Antonio et al. |
| 3,855,902 A | 12/1974 | Kirst et al. | 3,993,149 A | 11/1976 | Harvey |
| 3,857,399 A | 12/1974 | Zacouto et al. | 3,996,927 A | 12/1976 | Frank |
| 3,857,452 A | 12/1974 | Hartman | 3,996,962 A | 12/1976 | Sutherland |
| 3,857,745 A | 12/1974 | Grausch et al. | 4,003,141 A | 1/1977 | Le Roy |
| 3,858,581 A | 1/1975 | Kamen | 4,005,282 A | 1/1977 | Jennings |
| 3,863,622 A | 2/1975 | Buuck | 4,005,593 A | 2/1977 | Goldberg |
| 3,863,933 A | 2/1975 | Tredway | 4,006,735 A | 2/1977 | Hittman et al. |
| 3,867,950 A | 2/1975 | Fischell | 4,009,375 A | 2/1977 | White et al. |
| 3,868,008 A | 2/1975 | Brumbaugh | 4,009,591 A | 3/1977 | Hester |
| 3,868,679 A | 2/1975 | Arneson | 4,010,449 A | 3/1977 | Faggin et al. |
| 3,871,599 A | 3/1975 | Takada et al. | 4,014,319 A | 3/1977 | Favre et al. |
| 3,872,285 A | 3/1975 | Shum et al. | 4,014,321 A | 3/1977 | March |
| 3,874,388 A | 4/1975 | King et al. | 4,016,764 A | 4/1977 | Rice |
| 3,876,980 A | 4/1975 | Haemmig et al. | 4,017,329 A | 4/1977 | Larson |
| 3,878,908 A | 4/1975 | Andersson et al. | 4,018,134 A | 4/1977 | Linsinger et al. |
| 3,881,528 A | 5/1975 | Mackenzie | 4,022,190 A | 5/1977 | Meyer |
| 3,893,111 A | 7/1975 | Cotter | 4,024,864 A | 5/1977 | Davies et al. |
| 3,893,451 A | 7/1975 | Durand et al. | 4,025,912 A | 5/1977 | Rice |
| 3,895,681 A | 7/1975 | Griffin et al. | 4,026,276 A | 5/1977 | Chubbuck |
| 3,899,862 A | 8/1975 | Muys et al. | 4,027,661 A | 6/1977 | Lyon et al. |
| 3,904,234 A | 9/1975 | Hill et al. | 4,031,899 A | 6/1977 | Renirie et al. |
| 3,908,334 A | 9/1975 | Rychiger et al. | 4,036,775 A | 7/1977 | Trautvetter et al. |
| 3,908,461 A | 9/1975 | Turpen | 4,039,069 A | 8/1977 | Kwan et al. |
| 3,908,721 A | 9/1975 | McGahey et al. | 4,041,954 A | 8/1977 | Ohara et al. |
| 3,910,087 A | 10/1975 | Jones | 4,042,504 A | 8/1977 | Drori et al. |
| 3,912,168 A | 10/1975 | Mullins et al. | 4,045,345 A | 8/1977 | Drori et al. |
| 3,912,304 A | 10/1975 | Abildgaard et al. | 4,047,851 A | 9/1977 | Bender |
| 3,918,286 A | 11/1975 | Whitehead | 4,048,494 A | 9/1977 | Liesting et al. |
| 3,918,291 A | 11/1975 | Pauly et al. | 4,048,879 A | 9/1977 | Cox |
| 3,920,965 A | 11/1975 | Sohrwardy et al. | 4,049,004 A | 9/1977 | Walters |
| 3,921,682 A | 11/1975 | McGahey et al. | 4,051,338 A | 9/1977 | Harris, III |
| 3,922,951 A | 12/1975 | Linsinger et al. | 4,052,991 A | 10/1977 | Zacouto et al. |
| 3,923,060 A | 12/1975 | Ellinwood, Jr. | 4,055,074 A | 10/1977 | Thimons et al. |

| | | | | | |
|---|---|---|---|---|---|
| 4,055,175 A | 10/1977 | Clemens et al. | 4,191,187 A | 3/1980 | Wright et al. |
| 4,056,854 A | 11/1977 | Boretos et al. | 4,192,192 A | 3/1980 | Schnell |
| 4,058,007 A | 11/1977 | Exner et al. | 4,193,397 A | 3/1980 | Tucker et al. |
| 4,062,351 A | 12/1977 | Hastwell et al. | 4,204,547 A | 5/1980 | Allocca |
| 4,062,354 A | 12/1977 | Taylor et al. | 4,206,755 A | 6/1980 | Klein et al. |
| 4,062,360 A | 12/1977 | Bentley | 4,206,761 A | 6/1980 | Cosman |
| 4,063,439 A | 12/1977 | Besson et al. | 4,206,762 A | 6/1980 | Cosman |
| 4,064,882 A | 12/1977 | Johnson et al. | 4,207,903 A | 6/1980 | O'Neill |
| 4,070,239 A | 1/1978 | Bevilacqua | 4,212,074 A | 7/1980 | Kuno et al. |
| 4,072,047 A | 2/1978 | Reismuller et al. | 4,217,221 A | 8/1980 | Masso |
| 4,073,292 A | 2/1978 | Edelman | 4,217,588 A | 8/1980 | Freeny, Jr. |
| 4,075,099 A | 2/1978 | Pelton et al. | 4,220,189 A | 9/1980 | Marquez |
| 4,075,602 A | 2/1978 | Clothier | 4,221,219 A | 9/1980 | Tucker |
| 4,077,072 A | 3/1978 | Dezura et al. | 4,221,523 A | 9/1980 | Eberle |
| 4,077,394 A | 3/1978 | McCurdy | 4,222,377 A | 9/1980 | Burton |
| 4,077,405 A | 3/1978 | Haerten et al. | 4,223,837 A | 9/1980 | Gubbiotti et al. |
| 4,077,882 A | 3/1978 | Gangemi | 4,226,124 A | 10/1980 | Kersten et al. |
| 4,078,620 A | 3/1978 | Westlake et al. | 4,226,229 A | 10/1980 | Eckhart et al. |
| 4,080,653 A | 3/1978 | Barnes, Jr. et al. | 4,227,533 A | 10/1980 | Godfrey |
| 4,084,752 A | 4/1978 | Hagiwara et al. | 4,231,376 A | 11/1980 | Lyon et al. |
| 4,086,488 A | 4/1978 | Hill | 4,232,682 A | 11/1980 | Veth |
| 4,087,568 A | 5/1978 | Fay et al. | 4,237,900 A | 12/1980 | Schulman et al. |
| 4,088,417 A | 5/1978 | Kosmowski | 4,241,247 A | 12/1980 | Byrne et al. |
| 4,089,329 A | 5/1978 | Couvillon, Jr. et al. | 4,241,870 A | 12/1980 | Marcus |
| 4,090,802 A | 5/1978 | Bilz et al. | 4,245,593 A | 1/1981 | Stein |
| 4,092,719 A | 5/1978 | Salmon et al. | 4,246,877 A | 1/1981 | Kennedy |
| 4,092,925 A | 6/1978 | Fromson | 4,247,850 A | 1/1981 | Marcus |
| 4,096,866 A | 6/1978 | Fischell | 4,248,238 A | 2/1981 | Joseph et al. |
| 4,098,293 A | 7/1978 | Kramer et al. | 4,248,241 A | 2/1981 | Tacchi |
| 4,103,496 A | 8/1978 | Colamussi et al. | 4,256,094 A | 3/1981 | Kapp et al. |
| 4,106,370 A | 8/1978 | Kraus et al. | 4,256,118 A | 3/1981 | Nagel et al. |
| 4,107,689 A | 8/1978 | Jellinek | 4,262,343 A | 4/1981 | Claycomb |
| 4,107,995 A | 8/1978 | Ligman et al. | 4,262,632 A | 4/1981 | Hanton et al. |
| 4,108,148 A | 8/1978 | Cannon, III | 4,265,241 A | 5/1981 | Portner et al. |
| 4,108,575 A | 8/1978 | Schal et al. | 4,265,252 A | 5/1981 | Chubbuck et al. |
| 4,109,148 A | 8/1978 | Jaulmes et al. | 4,271,018 A | 6/1981 | Drori et al. |
| 4,109,518 A | 8/1978 | Dooley et al. | 4,273,070 A | 6/1981 | Hoefelmayr et al. |
| 4,109,644 A | 8/1978 | Kojima | 4,274,444 A | 6/1981 | Ruyak |
| 4,111,056 A | 9/1978 | Mastromatteo | 4,275,600 A | 6/1981 | Turner et al. |
| 4,111,629 A | 9/1978 | Nussbaumer et al. | 4,275,913 A | 6/1981 | Marcus |
| 4,114,424 A | 9/1978 | Johnson | 4,278,540 A | 7/1981 | Drori et al. |
| 4,114,606 A | 9/1978 | Seylar | 4,280,036 A | 7/1981 | Fukatsu et al. |
| 4,120,097 A | 10/1978 | Jeter | 4,280,775 A | 7/1981 | Wood |
| 4,120,134 A | 10/1978 | Scholle | 4,281,666 A | 8/1981 | Cosman |
| 4,121,635 A | 10/1978 | Hansel | 4,281,667 A | 8/1981 | Cosman |
| 4,123,310 A | 10/1978 | Varon et al. | 4,284,073 A | 8/1981 | Krause et al. |
| 4,124,023 A | 11/1978 | Fleischmann et al. | 4,285,770 A | 8/1981 | Chi et al. |
| 4,127,110 A | 11/1978 | Bullara | 4,291,699 A | 9/1981 | Geddes et al. |
| 4,130,169 A | 12/1978 | Denison | 4,295,963 A | 10/1981 | Drori et al. |
| 4,131,596 A | 12/1978 | Allen | 4,297,927 A | 11/1981 | Kuroda et al. |
| 4,133,355 A | 1/1979 | Mayer | 4,303,075 A | 12/1981 | Heilman et al. |
| 4,133,367 A | 1/1979 | Abell | 4,305,402 A | 12/1981 | Katims |
| 4,140,131 A | 2/1979 | Dutcher et al. | 4,312,374 A | 1/1982 | Drori et al. |
| 4,141,348 A | 2/1979 | Hittman | 4,314,480 A | 2/1982 | Becker |
| 4,141,349 A | 2/1979 | Ory et al. | 4,316,693 A | 2/1982 | Baxter et al. |
| 4,143,661 A | 3/1979 | LaForge et al. | 4,325,387 A | 4/1982 | Helfer |
| 4,146,029 A | 3/1979 | Ellinwood, Jr. | 4,327,804 A | 5/1982 | Reed |
| 4,147,161 A | 4/1979 | Ikebe et al. | 4,328,654 A | 5/1982 | Van Ginkel et al. |
| 4,148,096 A | 4/1979 | Haas et al. | 4,332,254 A | 6/1982 | Lundquist |
| 4,149,423 A | 4/1979 | Frosch et al. | 4,339,831 A | 7/1982 | Johnson |
| 4,151,823 A | 5/1979 | Grosse et al. | 4,342,218 A | 8/1982 | Fox |
| 4,153,085 A | 5/1979 | Adams | 4,342,308 A | 8/1982 | Trick |
| 4,156,422 A | 5/1979 | Hildebrandt et al. | 4,346,604 A | 8/1982 | Snook et al. |
| 4,160,448 A | 7/1979 | Jackson | 4,347,851 A | 9/1982 | Jundanian |
| 4,160,971 A | 7/1979 | Jones et al. | 4,350,647 A | 9/1982 | de la Cruz |
| 4,166,469 A | 9/1979 | Littleford | 4,350,970 A | 9/1982 | von Tomkewitsch et al. |
| 4,167,304 A | 9/1979 | Gelbke | 4,351,037 A | 9/1982 | Scherbatskoy |
| 4,167,952 A | 9/1979 | Reinicke | 4,351,116 A | 9/1982 | Scott, Jr. |
| 4,168,567 A | 9/1979 | Leguy et al. | 4,356,486 A | 10/1982 | Mount |
| 4,170,280 A | 10/1979 | Schwarz | 4,360,010 A | 11/1982 | Finney |
| 4,171,218 A | 10/1979 | Hoshino et al. | 4,360,277 A | 11/1982 | Daniel et al. |
| 4,183,124 A | 1/1980 | Hoffman | 4,361,153 A | 11/1982 | Slocum et al. |
| 4,183,247 A | 1/1980 | Allen et al. | 4,363,236 A | 12/1982 | Meyers |
| 4,185,641 A | 1/1980 | Minior et al. | 4,364,276 A | 12/1982 | Shimazoe et al. |
| 4,186,287 A | 1/1980 | Scott | 4,365,425 A | 12/1982 | Gotchel |
| 4,186,749 A | 2/1980 | Fryer | 4,368,937 A | 1/1983 | Palombo et al. |
| 4,186,751 A | 2/1980 | Fleischmann | 4,369,013 A | 1/1983 | Abildgaard et al. |
| 4,190,057 A | 2/1980 | Hill et al. | 4,373,527 A | 2/1983 | Fischell |
| 4,191,004 A | 3/1980 | Gmuer et al. | 4,376,523 A | 3/1983 | Goyen et al. |

| | | | | | | |
|---|---|---|---|---|---|---|
| 4,378,809 A | 4/1983 | Cosman | | 4,503,678 A | 3/1985 | Wimbush et al. |
| 4,380,427 A | 4/1983 | Hehl et al. | | 4,511,974 A | 4/1985 | Nakane et al. |
| 4,385,636 A | 5/1983 | Cosman | | 4,513,295 A | 4/1985 | Jones et al. |
| 4,386,422 A | 5/1983 | Mumby et al. | | 4,515,004 A | 5/1985 | Jaenson |
| 4,387,907 A | 6/1983 | Hiestand et al. | | 4,515,750 A | 5/1985 | Pardini et al. |
| 4,392,368 A | 7/1983 | Folkesson et al. | | 4,516,866 A | 5/1985 | Yamauchi et al. |
| 4,393,899 A | 7/1983 | Tsuji et al. | | 4,518,637 A | 5/1985 | Takeda et al. |
| 4,393,951 A | 7/1983 | Horst-Rudolf et al. | | 4,519,401 A | 5/1985 | Ko et al. |
| 4,395,232 A | 7/1983 | Koch | | 4,520,443 A | 5/1985 | Yuki et al. |
| 4,395,258 A | 7/1983 | Wang et al. | | 4,522,213 A | 6/1985 | Wallroth et al. |
| 4,395,916 A | 8/1983 | Martin | | 4,527,568 A | 7/1985 | Rickards et al. |
| 4,398,983 A | 8/1983 | Suzuki et al. | | 4,529,401 A | 7/1985 | Leslie et al. |
| 4,399,705 A | 8/1983 | Weiger et al. | | 4,531,526 A | 7/1985 | Genest |
| 4,399,707 A | 8/1983 | Wamstad | | 4,531,936 A | 7/1985 | Gordon |
| 4,399,809 A | 8/1983 | Baro et al. | | 4,536,000 A | 8/1985 | Rohm et al. |
| 4,399,821 A | 8/1983 | Bowers | | 4,537,005 A | 8/1985 | Hoyland et al. |
| 4,403,984 A | 9/1983 | Ash et al. | | 4,537,129 A | 8/1985 | Heinemann et al. |
| 4,404,968 A | 9/1983 | Evans, Sr. | | 4,538,616 A | 9/1985 | Rogoff |
| 4,404,974 A | 9/1983 | Titus | | 4,540,404 A | 9/1985 | Wolvek |
| 4,405,318 A | 9/1983 | Whitney et al. | | 4,542,461 A | 9/1985 | Eldridge et al. |
| 4,407,125 A | 10/1983 | Parsons et al. | | 4,544,369 A | 10/1985 | Skakoon et al. |
| 4,407,271 A | 10/1983 | Schiff | | 4,545,185 A | 10/1985 | Chikatani et al. |
| 4,407,296 A | 10/1983 | Anderson | | 4,546,524 A | 10/1985 | Kreft |
| 4,407,326 A | 10/1983 | Wilhelm | | 4,548,209 A | 10/1985 | Wielders et al. |
| 4,408,597 A | 10/1983 | Tenney, Jr. | | 4,552,150 A | 11/1985 | Zacouto et al. |
| 4,408,615 A | 10/1983 | Grossman | | 4,553,226 A | 11/1985 | Scherbatskoy |
| 4,415,071 A | 11/1983 | Butler et al. | | 4,556,063 A | 12/1985 | Thompson et al. |
| 4,416,282 A | 11/1983 | Saulson et al. | | 4,557,269 A | 12/1985 | Reynolds et al. |
| 4,418,899 A | 12/1983 | Zimmermann et al. | | 4,557,332 A | 12/1985 | Denison et al. |
| 4,419,393 A | 12/1983 | Hanson et al. | | 4,559,815 A | 12/1985 | Needham et al. |
| 4,421,505 A | 12/1983 | Schwartz | | 4,560,979 A | 12/1985 | Rosskopf et al. |
| 4,424,720 A | 1/1984 | Bucchianeri | | 4,561,442 A | 12/1985 | Vollmann et al. |
| 4,428,228 A | 1/1984 | Banzhaf et al. | | 4,562,751 A | 1/1986 | Nason et al. |
| 4,428,365 A | 1/1984 | Hakky et al. | | 4,563,175 A | 1/1986 | LaFond |
| 4,430,899 A | 2/1984 | Wessel et al. | | 4,565,116 A | 1/1986 | Hehl et al. |
| 4,431,009 A | 2/1984 | Marino, Jr. et al. | | 4,566,456 A | 1/1986 | Koning et al. |
| 4,431,365 A | 2/1984 | Sturtz, Jr. | | 4,569,623 A | 2/1986 | Goldmann |
| 4,432,363 A | 2/1984 | Kakegawa et al. | | 4,570,351 A | 2/1986 | Szanto et al. |
| 4,435,173 A | 3/1984 | Siposs et al. | | 4,571,161 A | 2/1986 | Leblanc et al. |
| 4,439,186 A | 3/1984 | Kuhl et al. | | 4,571,995 A | 2/1986 | Timme |
| 4,441,491 A | 4/1984 | Evans, Sr. | | 4,573,835 A | 3/1986 | Eckardt et al. |
| 4,441,501 A | 4/1984 | Parent | | 4,574,792 A | 3/1986 | Trick |
| 4,444,194 A | 4/1984 | Burcham | | 4,576,181 A | 3/1986 | Wallace et al. |
| 4,444,498 A | 4/1984 | Heinemann | | 4,576,183 A | 3/1986 | Plicchi et al. |
| 4,445,385 A | 5/1984 | Endo | | 4,577,512 A | 3/1986 | Lowenheck et al. |
| 4,446,711 A | 5/1984 | Valente | | 4,581,018 A | 4/1986 | Jassawalla et al. |
| 4,447,224 A | 5/1984 | DeCant, Jr. et al. | | 4,581,915 A | 4/1986 | Haulsee et al. |
| 4,449,493 A | 5/1984 | Kopec et al. | | 4,587,840 A | 5/1986 | Dobler et al. |
| 4,450,811 A | 5/1984 | Ichikawa et al. | | 4,589,805 A | 5/1986 | Duffner et al. |
| 4,451,033 A | 5/1984 | Nestegard | | 4,592,339 A | 6/1986 | Kuzmak et al. |
| 4,453,537 A | 6/1984 | Spitzer | | 4,592,340 A | 6/1986 | Boyles |
| 4,453,578 A | 6/1984 | Wilder | | 4,593,703 A | 6/1986 | Cosman |
| 4,460,835 A | 7/1984 | Masuoka et al. | | 4,595,228 A | 6/1986 | Chu |
| 4,464,170 A | 8/1984 | Clemens et al. | | 4,596,563 A | 6/1986 | Pande |
| 4,465,015 A | 8/1984 | Osta et al. | | 4,599,943 A | 7/1986 | Kobler et al. |
| 4,465,474 A | 8/1984 | Mardorf et al. | | 4,600,855 A | 7/1986 | Strachan et al. |
| 4,466,290 A | 8/1984 | Frick | | 4,602,541 A | 7/1986 | Benzinger et al. |
| 4,468,172 A | 8/1984 | Dixon et al. | | 4,604,089 A | 8/1986 | Santangelo et al. |
| 4,468,762 A | 8/1984 | Jurgens et al. | | 4,605,354 A | 8/1986 | Daly |
| 4,469,365 A | 9/1984 | Marcus et al. | | 4,606,419 A | 8/1986 | Perini |
| 4,471,182 A | 9/1984 | Wielgos et al. | | 4,606,478 A | 8/1986 | Hack et al. |
| 4,471,786 A | 9/1984 | Inagaki et al. | | 4,610,256 A | 9/1986 | Wallace |
| 4,473,067 A | 9/1984 | Schiff | | 4,614,137 A | 9/1986 | Jones |
| 4,473,078 A | 9/1984 | Angel | | 4,617,016 A | 10/1986 | Blomberg et al. |
| 4,476,721 A | 10/1984 | Hochreuther et al. | | 4,618,861 A | 10/1986 | Gettens et al. |
| 4,478,213 A | 10/1984 | Redding | | 4,620,807 A | 11/1986 | Polit |
| 4,478,538 A | 10/1984 | Kakino et al. | | 4,621,331 A | 11/1986 | Iwata et al. |
| 4,483,196 A | 11/1984 | Kurtz et al. | | 4,622,871 A | 11/1986 | Van Sickle et al. |
| 4,484,135 A | 11/1984 | Ishihara et al. | | 4,626,462 A | 12/1986 | Kober et al. |
| 4,485,813 A | 12/1984 | Anderson et al. | | 4,633,304 A | 12/1986 | Nagasaki et al. |
| 4,489,916 A | 12/1984 | Stevens | | 4,633,878 A | 1/1987 | Bombardieri et al. |
| 4,492,632 A | 1/1985 | Mattson | | 4,635,182 A | 1/1987 | Hintz |
| 4,494,411 A | 1/1985 | Koschke et al. | | 4,637,736 A | 1/1987 | Andeen et al. |
| 4,494,950 A | 1/1985 | Fischell | | 4,638,665 A | 1/1987 | Benson et al. |
| 4,497,176 A | 2/1985 | Rubin et al. | | 4,644,246 A | 2/1987 | Knapen et al. |
| 4,497,201 A | 2/1985 | Allen et al. | | 4,646,553 A | 3/1987 | Tufte et al. |
| 4,499,394 A | 2/1985 | Koal | | 4,648,363 A | 3/1987 | Kronich |
| 4,499,691 A | 2/1985 | Karazim et al. | | 4,648,406 A | 3/1987 | Miller |
| 4,499,750 A | 2/1985 | Gerber et al. | | 4,658,358 A | 4/1987 | Leach et al. |

| | | | | | |
|---|---|---|---|---|---|
| 4,658,760 A | 4/1987 | Zebuhr | 4,807,321 A | 2/1989 | Grasselli et al. |
| 4,660,568 A | 4/1987 | Cosman | 4,808,167 A | 2/1989 | Mann et al. |
| 4,665,511 A | 5/1987 | Rodney et al. | 4,812,823 A | 3/1989 | Dickerson |
| 4,665,896 A | 5/1987 | LaForge et al. | 4,819,656 A | 4/1989 | Spector |
| 4,669,484 A | 6/1987 | Masters | 4,820,265 A | 4/1989 | DeSatnick et al. |
| 4,672,974 A | 6/1987 | Lee | 4,820,953 A | 4/1989 | Saubolle et al. |
| 4,674,457 A | 6/1987 | Berger et al. | 4,821,167 A | 4/1989 | Wiebe |
| 4,674,546 A | 6/1987 | Fournier et al. | 4,821,723 A | 4/1989 | Baker, Jr. et al. |
| 4,678,408 A | 7/1987 | Nason et al. | 4,823,779 A | 4/1989 | Daly et al. |
| 4,681,559 A | 7/1987 | Hooven | 4,830,006 A | 5/1989 | Haluska et al. |
| 4,683,850 A | 8/1987 | Bauder et al. | 4,832,034 A | 5/1989 | Pizziconi et al. |
| 4,685,463 A | 8/1987 | Williams | 4,833,384 A | 5/1989 | Munro et al. |
| 4,685,469 A | 8/1987 | Keller et al. | 4,834,731 A | 5/1989 | Nowak et al. |
| 4,685,903 A | 8/1987 | Cable et al. | 4,838,857 A | 6/1989 | Strowe et al. |
| 4,686,987 A | 8/1987 | Salo et al. | 4,840,068 A | 6/1989 | Mayhew, Jr. |
| 4,687,530 A | 8/1987 | Berscheid et al. | 4,840,350 A | 6/1989 | Cook et al. |
| 4,689,979 A | 9/1987 | Otsuka et al. | 4,844,002 A | 7/1989 | Yasui et al. |
| 4,691,694 A | 9/1987 | Boyd et al. | 4,846,153 A | 7/1989 | Berci |
| 4,691,710 A | 9/1987 | Dickens et al. | 4,846,191 A | 7/1989 | Brockway et al. |
| 4,693,253 A | 9/1987 | Adams | 4,846,664 A | 7/1989 | Hehl et al. |
| 4,695,237 A | 9/1987 | Inaba et al. | 4,854,328 A | 8/1989 | Pollack |
| 4,696,189 A | 9/1987 | Hochreuther et al. | 4,863,470 A | 9/1989 | Carter |
| 4,697,574 A | 10/1987 | Karcher et al. | 4,865,587 A | 9/1989 | Walling |
| 4,698,038 A | 10/1987 | Key et al. | 4,867,160 A | 9/1989 | Schaldach et al. |
| 4,700,497 A | 10/1987 | Sato et al. | 4,867,498 A | 9/1989 | Delphia et al. |
| 4,700,610 A | 10/1987 | Bauer et al. | 4,867,618 A | 9/1989 | Brohammer |
| 4,701,143 A | 10/1987 | Key et al. | 4,869,252 A | 9/1989 | Gilli |
| 4,703,756 A | 11/1987 | Gough et al. | 4,870,258 A | 9/1989 | Mochizuki et al. |
| 4,705,507 A | 11/1987 | Boyles | 4,871,351 A | 10/1989 | Feingold et al. |
| 4,706,948 A | 11/1987 | Kroecher | 4,872,483 A | 10/1989 | Shah |
| 4,712,562 A | 12/1987 | Ohayon et al. | 4,872,869 A | 10/1989 | Johns |
| 4,718,425 A | 1/1988 | Tanaka et al. | 4,873,677 A | 10/1989 | Sakamoto et al. |
| 4,722,348 A | 2/1988 | Ligtenberg et al. | 4,875,483 A | 10/1989 | Vollmann et al. |
| 4,724,806 A | 2/1988 | Hartwig et al. | 4,880,004 A | 11/1989 | Baker, Jr. et al. |
| 4,724,830 A | 2/1988 | Fischell | 4,882,678 A | 11/1989 | Hollis et al. |
| 4,725,826 A | 2/1988 | Hunter | 4,886,392 A | 12/1989 | Iio et al. |
| 4,728,479 A | 3/1988 | Merkovsky | 4,895,151 A | 1/1990 | Grevis et al. |
| 4,729,517 A | 3/1988 | Krokor et al. | 4,896,594 A | 1/1990 | Baur et al. |
| 4,730,188 A | 3/1988 | Milheiser | 4,898,158 A | 2/1990 | Daly et al. |
| 4,730,420 A | 3/1988 | Stratmann et al. | 4,898,578 A | 2/1990 | Rubalcaba, Jr. |
| 4,730,619 A | 3/1988 | Koning et al. | 4,899,751 A | 2/1990 | Cohen |
| 4,731,058 A | 3/1988 | Doan | 4,899,752 A | 2/1990 | Cohen |
| 4,735,205 A | 4/1988 | Chachques et al. | 4,902,277 A | 2/1990 | Mathies et al. |
| 4,738,267 A | 4/1988 | Lazorthes et al. | 4,903,701 A | 2/1990 | Moore et al. |
| 4,738,268 A | 4/1988 | Kipnis | 4,909,678 A | 3/1990 | Kakimoto et al. |
| 4,741,345 A | 5/1988 | Matthews et al. | 4,913,147 A | 4/1990 | Fahlstrom et al. |
| 4,741,732 A | 5/1988 | Crankshaw et al. | 4,919,143 A | 4/1990 | Ayers |
| 4,743,129 A | 5/1988 | Keryhuel et al. | 4,924,872 A | 5/1990 | Frank |
| 4,745,541 A | 5/1988 | Vaniglia et al. | 4,926,903 A | 5/1990 | Kawai et al. |
| 4,746,830 A | 5/1988 | Holland | 4,932,406 A | 6/1990 | Berkovits |
| 4,750,495 A | 6/1988 | Moore et al. | 4,934,369 A | 6/1990 | Maxwell |
| 4,752,115 A | 6/1988 | Murray, Jr. et al. | 4,936,304 A | 6/1990 | Kresh et al. |
| 4,752,658 A | 6/1988 | Mack | 4,940,037 A | 7/1990 | Eckert et al. |
| 4,757,463 A | 7/1988 | Ballou et al. | 4,941,718 A | 7/1990 | Alexander, III et al. |
| 4,759,386 A | 7/1988 | Grouw, III | 4,942,004 A | 7/1990 | Catanzaro |
| 4,763,649 A | 8/1988 | Merrick | 4,944,050 A | 7/1990 | Shames et al. |
| 4,765,001 A | 8/1988 | Smith | 4,944,298 A | 7/1990 | Sholder |
| 4,767,406 A | 8/1988 | Wadham et al. | 4,944,307 A | 7/1990 | Hon et al. |
| 4,769,001 A | 9/1988 | Prince | 4,945,761 A | 8/1990 | Lessi et al. |
| 4,772,896 A | 9/1988 | Nakatsu et al. | 4,949,724 A | 8/1990 | Mahutte et al. |
| 4,773,401 A | 9/1988 | Citak et al. | 4,952,205 A | 8/1990 | Mauerer et al. |
| 4,774,950 A | 10/1988 | Cohen | 4,952,928 A | 8/1990 | Carroll et al. |
| 4,774,955 A | 10/1988 | Jones | 4,953,563 A | 9/1990 | Kaiser et al. |
| 4,777,953 A | 10/1988 | Ash et al. | 4,954,677 A | 9/1990 | Alberter et al. |
| 4,779,626 A | 10/1988 | Peel et al. | 4,958,630 A | 9/1990 | Rosenbluth et al. |
| 4,781,192 A | 11/1988 | Demer | 4,958,645 A | 9/1990 | Cadell et al. |
| 4,782,826 A | 11/1988 | Fogarty | 4,960,424 A | 10/1990 | Grooters |
| 4,783,106 A | 11/1988 | Nutter | 4,960,966 A | 10/1990 | Evans et al. |
| 4,788,847 A | 12/1988 | Sterghos | 4,967,585 A | 11/1990 | Grimaldo |
| 4,791,318 A | 12/1988 | Lewis et al. | 4,967,761 A | 11/1990 | Nathanielsz |
| 4,794,803 A | 1/1989 | Osterhout et al. | 4,970,823 A | 11/1990 | Chen et al. |
| 4,796,641 A | 1/1989 | Mills et al. | 4,971,251 A | 11/1990 | Dobrick et al. |
| 4,798,211 A | 1/1989 | Goor et al. | 4,977,896 A | 12/1990 | Robinson et al. |
| 4,798,227 A | 1/1989 | Goodwin | 4,978,335 A | 12/1990 | Arthur, III |
| 4,799,491 A | 1/1989 | Eckerle | 4,978,338 A | 12/1990 | Melsky et al. |
| 4,799,625 A | 1/1989 | Weaver, Jr. et al. | 4,979,730 A | 12/1990 | Holbrook et al. |
| 4,802,488 A | 2/1989 | Eckerle | 4,980,671 A | 12/1990 | McCurdy |
| 4,803,987 A | 2/1989 | Calfee et al. | 4,981,141 A | 1/1991 | Segalowitz |
| 4,804,368 A | 2/1989 | Skakoon et al. | 4,981,173 A | 1/1991 | Perkins et al. |

| Patent No. | Date | Inventor |
|---|---|---|
| 4,981,426 A | 1/1991 | Aoki et al. |
| 4,987,897 A | 1/1991 | Funke et al. |
| 4,988,337 A | 1/1991 | Ito et al. |
| 4,992,794 A | 2/1991 | Brouwers et al. |
| 4,997,556 A | 3/1991 | Yano et al. |
| 5,001,528 A | 3/1991 | Bahraman |
| 5,003,807 A | 4/1991 | Terrell et al. |
| 5,003,975 A | 4/1991 | Hafelfinger et al. |
| 5,003,976 A | 4/1991 | Alt et al. |
| 5,004,472 A | 4/1991 | Wallace |
| 5,004,873 A | 4/1991 | Schnut |
| 5,005,574 A | 4/1991 | Fearnot et al. |
| 5,005,586 A | 4/1991 | Lahr |
| 5,006,844 A | 4/1991 | Ohta et al. |
| 5,007,401 A | 4/1991 | Grohn et al. |
| 5,007,430 A | 4/1991 | Dardik |
| 5,007,919 A | 4/1991 | Silva et al. |
| 5,009,662 A | 4/1991 | Wallace et al. |
| 5,010,893 A | 4/1991 | Sholder |
| 5,012,286 A | 4/1991 | Kawano et al. |
| 5,012,810 A | 5/1991 | Strand et al. |
| 5,013,292 A | 5/1991 | Lemay et al. |
| 5,014,040 A | 5/1991 | Weaver et al. |
| 5,019,032 A | 5/1991 | Robertson |
| 5,019,041 A | 5/1991 | Robinson et al. |
| 5,020,845 A | 6/1991 | Falcoff et al. |
| 5,021,046 A | 6/1991 | Wallace |
| 5,022,395 A | 6/1991 | Russie |
| 5,024,965 A | 6/1991 | Chang et al. |
| 5,026,180 A | 6/1991 | Tajima et al. |
| 5,026,360 A | 6/1991 | Johnsen et al. |
| 5,028,918 A | 7/1991 | Giles et al. |
| 5,032,822 A | 7/1991 | Sweet |
| 5,036,869 A | 8/1991 | Inahara et al. |
| 5,038,800 A | 8/1991 | Oba et al. |
| 5,041,086 A | 8/1991 | Koenig et al. |
| 5,041,826 A | 8/1991 | Milheiser |
| 5,042,503 A | 8/1991 | Torok et al. |
| 5,044,770 A | 9/1991 | Haghkar |
| 5,046,661 A | 9/1991 | Kimura et al. |
| 5,048,060 A | 9/1991 | Arai et al. |
| 5,050,922 A | 9/1991 | Falcoff |
| 5,052,910 A | 10/1991 | Hehl et al. |
| 5,053,008 A | 10/1991 | Bajaj |
| 5,057,078 A | 10/1991 | Foote et al. |
| 5,058,583 A | 10/1991 | Geddes et al. |
| 5,061,239 A | 10/1991 | Shiels |
| 5,062,052 A | 10/1991 | Sparer et al. |
| 5,062,053 A | 10/1991 | Shirai et al. |
| 5,062,559 A | 11/1991 | Falcoff |
| 5,064,974 A | 11/1991 | Vigneau et al. |
| 5,067,960 A | 11/1991 | Grandjean et al. |
| 5,068,779 A | 11/1991 | Sullivan et al. |
| 5,069,680 A | 12/1991 | Grandjean et al. |
| 5,077,102 A | 12/1991 | Chong |
| 5,077,870 A | 1/1992 | Melbye et al. |
| 5,078,139 A | 1/1992 | Strand et al. |
| 5,082,006 A | 1/1992 | Jonasson et al. |
| 5,083,563 A | 1/1992 | Collins et al. |
| 5,084,699 A | 1/1992 | DeMichele |
| 5,085,224 A | 2/1992 | Galen et al. |
| 5,085,258 A | 2/1992 | Fink, Jr. et al. |
| 5,089,673 A | 2/1992 | Strzodka et al. |
| 5,089,979 A | 2/1992 | McEachern et al. |
| 5,090,446 A * | 2/1992 | Hunter et al. .......... 137/540 |
| 5,095,309 A | 3/1992 | Troyk et al. |
| 5,096,271 A | 3/1992 | Portman |
| 5,097,831 A | 3/1992 | Lekholm |
| 5,098,384 A | 3/1992 | Abrams |
| 5,103,832 A | 4/1992 | Jackson |
| 5,105,810 A | 4/1992 | Collins et al. |
| 5,107,850 A | 4/1992 | Olive |
| 5,112,344 A | 5/1992 | Petros et al. |
| 5,113,859 A | 5/1992 | Funke et al. |
| 5,113,869 A | 5/1992 | Nappholz et al. |
| 5,115,676 A | 5/1992 | Lee |
| 5,117,825 A | 6/1992 | Grevious |
| 5,121,777 A | 6/1992 | Leininger et al. |
| 5,127,451 A | 7/1992 | Fink, Jr. et al. |
| 5,129,394 A | 7/1992 | Mehra |
| 5,129,806 A | 7/1992 | Hehl et al. |
| 5,131,145 A | 7/1992 | Badoureaux et al. |
| 5,131,388 A | 7/1992 | Pless et al. |
| 5,133,358 A | 7/1992 | Gustafson et al. |
| 5,135,488 A | 8/1992 | Foote et al. |
| 5,139,484 A | 8/1992 | Hazon et al. |
| 5,144,949 A | 9/1992 | Olson |
| 5,148,580 A | 9/1992 | Dyckow et al. |
| 5,148,695 A | 9/1992 | Ellis |
| 5,152,770 A | 10/1992 | Bengmark et al. |
| 5,152,776 A | 10/1992 | Pinchuk |
| 5,154,170 A | 10/1992 | Bennett et al. |
| 5,154,171 A | 10/1992 | Chirife et al. |
| 5,154,693 A | 10/1992 | East et al. |
| 5,156,972 A | 10/1992 | Issachar et al. |
| 5,158,078 A | 10/1992 | Bennett et al. |
| 5,163,429 A | 11/1992 | Cohen |
| 5,167,615 A | 12/1992 | East et al. |
| 5,168,757 A | 12/1992 | Rabenau et al. |
| 5,168,982 A | 12/1992 | Hakanen et al. |
| 5,171,299 A | 12/1992 | Heitzmann et al. |
| 5,173,873 A | 12/1992 | Wu et al. |
| 5,174,286 A | 12/1992 | Chirife et al. |
| 5,174,291 A | 12/1992 | Schoonen et al. |
| 5,176,502 A | 1/1993 | Sanderson et al. |
| 5,178,197 A | 1/1993 | Healy |
| 5,181,423 A | 1/1993 | Philipps et al. |
| 5,181,517 A | 1/1993 | Hickey |
| 5,184,132 A | 2/1993 | Baird |
| 5,184,614 A | 2/1993 | Collins et al. |
| 5,184,619 A | 2/1993 | Austin |
| 5,185,535 A | 2/1993 | Farb et al. |
| 5,186,224 A | 2/1993 | Schirmacher et al. |
| 5,188,106 A | 2/1993 | Nappholz et al. |
| 5,188,604 A | 2/1993 | Orth |
| 5,192,314 A | 3/1993 | Daskalakis |
| 5,195,362 A | 3/1993 | Eason |
| 5,197,322 A | 3/1993 | Indravudh |
| 5,199,427 A | 4/1993 | Strickland |
| 5,199,428 A | 4/1993 | Obel et al. |
| 5,201,753 A | 4/1993 | Lampropoulos et al. |
| 5,204,670 A | 4/1993 | Stinton |
| 5,207,429 A | 5/1993 | Walmsley et al. |
| 5,209,223 A | 5/1993 | McGorry et al. |
| 5,209,732 A | 5/1993 | Lampropoulos et al. |
| 5,211,129 A | 5/1993 | Taylor et al. |
| 5,211,161 A | 5/1993 | Stef et al. |
| 5,212,476 A | 5/1993 | Maloney |
| 5,213,331 A | 5/1993 | Avanzini |
| 5,215,523 A | 6/1993 | Williams et al. |
| 5,218,343 A | 6/1993 | Stobbe et al. |
| 5,218,957 A | 6/1993 | Strickland |
| 5,226,429 A | 7/1993 | Kuzmak |
| 5,226,604 A | 7/1993 | Seiffert et al. |
| 5,230,694 A | 7/1993 | Rosenblum |
| 5,233,985 A | 8/1993 | Hudrlik |
| 5,235,326 A | 8/1993 | Beigel et al. |
| 5,244,269 A | 9/1993 | Harriehausen et al. |
| 5,244,461 A | 9/1993 | Derlien et al. |
| 5,246,008 A | 9/1993 | Mueller et al. |
| 5,249,858 A | 10/1993 | Nusser |
| 5,250,020 A | 10/1993 | Bley |
| 5,254,096 A | 10/1993 | Rondelet et al. |
| 5,256,157 A | 10/1993 | Samiotes et al. |
| 5,263,244 A | 11/1993 | Centa et al. |
| 5,263,981 A | 11/1993 | Polyak et al. |
| 5,267,940 A | 12/1993 | Moulder |
| 5,267,942 A | 12/1993 | Saperston |
| 5,269,891 A | 12/1993 | Colin et al. |
| 5,271,395 A | 12/1993 | Wahlstrand et al. |
| 5,274,859 A | 1/1994 | Redman et al. |
| 5,280,789 A | 1/1994 | Potts |
| 5,282,839 A | 2/1994 | Roline et al. |
| 5,282,840 A | 2/1994 | Hudrlik |
| 5,291,894 A | 3/1994 | Nagy et al. |
| 5,292,219 A | 3/1994 | Merin et al. |
| 5,295,967 A | 3/1994 | Rondelet et al. |
| 5,298,022 A | 3/1994 | Bernardi et al. |

| | | | | | | |
|---|---|---|---|---|---|---|
| 5,298,884 A | 3/1994 | Gilmore et al. | | 5,507,785 A | 4/1996 | Deno |
| 5,300,093 A | 4/1994 | Koestner et al. | | 5,509,888 A | 4/1996 | Miller |
| 5,300,120 A | 4/1994 | Knapp et al. | | 5,509,891 A | 4/1996 | DeRidder |
| 5,304,112 A | 4/1994 | Mrklas et al. | | 5,513,945 A | 5/1996 | Hartmann et al. |
| 5,305,923 A | 4/1994 | Kirschner et al. | | 5,514,103 A | 5/1996 | Srisathapat et al. |
| 5,312,443 A | 5/1994 | Adams et al. | | 5,518,504 A | 5/1996 | Polyak |
| 5,312,452 A | 5/1994 | Salo | | 5,520,606 A | 5/1996 | Schoolman et al. |
| 5,312,453 A | 5/1994 | Shelton et al. | | 5,523,740 A | 6/1996 | Burgmann et al. |
| 5,313,953 A | 5/1994 | Yomtov et al. | | 5,534,018 A | 7/1996 | Wahlstrand et al. |
| 5,314,451 A | 5/1994 | Mulier | | 5,535,752 A | 7/1996 | Halperin et al. |
| 5,314,457 A | 5/1994 | Jeutter et al. | | 5,538,005 A | 7/1996 | Harrison et al. |
| 5,324,315 A | 6/1994 | Grevious | | 5,541,857 A | 7/1996 | Walter et al. |
| 5,325,834 A | 7/1994 | Ballheimer et al. | | 5,545,140 A | 8/1996 | Conero et al. |
| 5,326,249 A | 7/1994 | Weissfloch et al. | | 5,545,151 A | 8/1996 | O'Connor et al. |
| 5,328,460 A | 7/1994 | Lord et al. | | 5,545,186 A | 8/1996 | Olson et al. |
| 5,330,511 A | 7/1994 | Boute et al. | | 5,545,214 A | 8/1996 | Stevens |
| 5,337,750 A | 8/1994 | Walloch | | 5,547,470 A | 8/1996 | Johnson et al. |
| 5,341,430 A | 8/1994 | Aulia et al. | | 5,551,427 A | 9/1996 | Altman |
| 5,342,401 A | 8/1994 | Spano et al. | | 5,551,439 A | 9/1996 | Hickey |
| 5,342,406 A | 8/1994 | Thompson | | 5,554,185 A | 9/1996 | Block et al. |
| 5,344,388 A | 9/1994 | Maxwell et al. | | 5,558,644 A | 9/1996 | Boyd et al. |
| 5,347,476 A | 9/1994 | McBean, Sr. | | 5,564,434 A | 10/1996 | Halperin et al. |
| 5,348,210 A | 9/1994 | Linzell et al. | | 5,575,770 A | 11/1996 | Melsky et al. |
| 5,348,536 A | 9/1994 | Young et al. | | 5,584,803 A | 12/1996 | Stevens et al. |
| 5,350,413 A | 9/1994 | Miller et al. | | 5,586,629 A | 12/1996 | Shoberg et al. |
| 5,352,180 A | 10/1994 | Candelon et al. | | 5,593,430 A | 1/1997 | Renger |
| 5,353,622 A | 10/1994 | Theener | | 5,594,665 A | 1/1997 | Walter et al. |
| 5,353,800 A | 10/1994 | Pohndorf et al. | | 5,596,986 A | 1/1997 | Goldfarb |
| 5,354,200 A | 10/1994 | Klein et al. | | 5,597,284 A | 1/1997 | Weltlich et al. |
| 5,354,316 A | 10/1994 | Keimel | | 5,610,083 A | 3/1997 | Chan et al. |
| 5,354,319 A | 10/1994 | Wyborny et al. | | 5,611,768 A | 3/1997 | Tutrone, Jr. |
| 5,360,407 A | 11/1994 | Leonard et al. | | 5,612,497 A | 3/1997 | Walter et al. |
| 5,365,462 A | 11/1994 | McBean, Sr. | | 5,615,671 A | 4/1997 | Schoonen et al. |
| 5,365,619 A | 11/1994 | Solomon | | 5,619,991 A | 4/1997 | Sloane |
| 5,365,985 A | 11/1994 | Todd et al. | | 5,625,946 A | 5/1997 | Wildeson et al. |
| 5,368,040 A | 11/1994 | Carney | | 5,626,623 A | 5/1997 | Kieval et al. |
| 5,370,665 A | 12/1994 | Hudrlik | | 5,626,630 A | 5/1997 | Markowitz et al. |
| 5,373,852 A | 12/1994 | Harrison et al. | | 5,630,836 A | 5/1997 | Prem et al. |
| 5,375,073 A | 12/1994 | McBean | | 5,634,255 A | 6/1997 | Bishop et al. |
| 5,377,128 A | 12/1994 | McBean | | 5,637,083 A | 6/1997 | Bertrand et al. |
| 5,378,231 A | 1/1995 | Johnson et al. | | 5,643,207 A | 7/1997 | Rise |
| 5,382,232 A | 1/1995 | Hague et al. | | 5,645,116 A | 7/1997 | McDonald |
| 5,383,915 A | 1/1995 | Adams | | 5,650,766 A | 7/1997 | Burgmann et al. |
| 5,388,578 A | 2/1995 | Yomtov et al. | | 5,673,585 A | 10/1997 | Bishop et al. |
| 5,388,586 A | 2/1995 | Lee et al. | | 5,676,690 A | 10/1997 | Noren et al. |
| 5,388,831 A | 2/1995 | Quadri et al. | | 5,681,285 A | 10/1997 | Ford et al. |
| 5,394,909 A | 3/1995 | Mitchell et al. | | 5,686,831 A | 11/1997 | Vandervalk et al. |
| 5,402,944 A | 4/1995 | Pape et al. | | 5,687,734 A | 11/1997 | Dempsey et al. |
| 5,406,957 A | 4/1995 | Tansey | | 5,693,076 A | 12/1997 | Kaemmerer |
| 5,409,009 A | 4/1995 | Olson | | 5,702,368 A | 12/1997 | Stevens et al. |
| 5,411,031 A | 5/1995 | Yomtov | | 5,702,427 A | 12/1997 | Ecker et al. |
| 5,411,551 A | 5/1995 | Winston et al. | | 5,702,431 A | 12/1997 | Wang et al. |
| 5,411,552 A | 5/1995 | Andersen et al. | | 5,704,352 A | 1/1998 | Tremblay et al. |
| 5,416,372 A | 5/1995 | Ljungstroem et al. | | 5,715,786 A | 2/1998 | Seiberth et al. |
| 5,417,226 A | 5/1995 | Juma | | 5,715,837 A | 2/1998 | Chen |
| 5,417,717 A | 5/1995 | Salo et al. | | 5,720,436 A | 2/1998 | Buschor et al. |
| 5,425,362 A | 6/1995 | Siker et al. | | 5,730,101 A | 3/1998 | Aupperle et al. |
| 5,431,171 A | 7/1995 | Harrison et al. | | 5,732,710 A | 3/1998 | Rabinovich et al. |
| 5,431,694 A | 7/1995 | Snaper et al. | | 5,733,313 A | 3/1998 | Barreras, Sr. et al. |
| 5,433,694 A | 7/1995 | Lim et al. | | 5,738,652 A | 4/1998 | Boyd et al. |
| 5,437,605 A | 8/1995 | Helmy et al. | | 5,742,233 A | 4/1998 | Hoffman et al. |
| 5,443,215 A | 8/1995 | Fackler | | 5,743,267 A | 4/1998 | Nikolic et al. |
| 5,447,519 A | 9/1995 | Peterson | | 5,749,369 A | 5/1998 | Rabinovich et al. |
| 5,449,368 A | 9/1995 | Kuzmak | | 5,749,909 A | 5/1998 | Schroeppel et al. |
| 5,456,690 A | 10/1995 | Duong-Van | | 5,755,687 A | 5/1998 | Donlon |
| 5,461,390 A | 10/1995 | Hoshen | | 5,755,748 A | 5/1998 | Borza et al. |
| 5,464,435 A | 11/1995 | Neumann | | 5,765,568 A | 6/1998 | Sweezer, Jr. et al. |
| 5,467,627 A | 11/1995 | Smith et al. | | 5,769,812 A | 6/1998 | Stevens et al. |
| 5,474,226 A | 12/1995 | Joseph | | 5,771,903 A | 6/1998 | Jakobsson |
| 5,479,818 A | 1/1996 | Walter et al. | | 5,782,774 A | 7/1998 | Shmulewitz |
| 5,482,049 A | 1/1996 | Addiss et al. | | 5,787,520 A | 8/1998 | Dunbar |
| 5,487,760 A | 1/1996 | Villafana | | 5,791,344 A | 8/1998 | Schulman et al. |
| 5,493,738 A | 2/1996 | Sanderson et al. | | 5,792,094 A | 8/1998 | Stevens et al. |
| 5,494,036 A | 2/1996 | Uber, III et al. | | 5,792,179 A | 8/1998 | Sideris |
| 5,494,193 A | 2/1996 | Kirschner et al. | | 5,795,325 A | 8/1998 | Valley et al. |
| 5,504,474 A | 4/1996 | Libman et al. | | 5,796,827 A | 8/1998 | Coppersmith et al. |
| 5,505,916 A | 4/1996 | Berry, Jr. | | 5,800,375 A | 9/1998 | Sweezer et al. |
| 5,507,412 A | 4/1996 | Ebert et al. | | 5,807,265 A | 9/1998 | Itoigawa et al. |
| 5,507,737 A | 4/1996 | Palmskog et al. | | 5,807,336 A | 9/1998 | Russo et al. |

| | | | | | | |
|---|---|---|---|---|---|---|
| 5,810,015 | A | 9/1998 | Flaherty | 6,366,817 B1 | 4/2002 | Kung |
| 5,810,757 | A | 9/1998 | Sweezer, Jr. et al. | 6,379,308 B1 | 4/2002 | Brockway et al. |
| 5,814,016 | A | 9/1998 | Valley et al. | 6,379,380 B1 | 4/2002 | Satz |
| 5,817,093 | A | 10/1998 | Williamson, IV et al. | 6,398,752 B1 | 6/2002 | Sweezer, Jr. et al. |
| 5,833,603 | A | 11/1998 | Kovacs et al. | 6,409,674 B1 | 6/2002 | Brockway et al. |
| 5,836,300 | A | 11/1998 | Mault | 6,423,031 B1 | 7/2002 | Donlon |
| 5,836,886 | A | 11/1998 | Itoigawa et al. | 6,430,444 B1 | 8/2002 | Borza et al. |
| 5,840,081 | A | 11/1998 | Andersen et al. | 6,431,175 B1 | 8/2002 | Penner et al. |
| 5,849,225 | A | 12/1998 | Ebina et al. | 6,432,040 B1 | 8/2002 | Meah |
| 5,855,597 | A | 1/1999 | Jayaraman et al. | 6,443,887 B1 | 9/2002 | Derus et al. |
| 5,855,601 | A | 1/1999 | Bessler et al. | 6,443,893 B1 | 9/2002 | Schnakenberg et al. |
| 5,860,938 | A | 1/1999 | Lafontaine et al. | 6,450,173 B1 | 9/2002 | Forsell et al. |
| 5,861,018 | A | 1/1999 | Feierbach | 6,450,946 B1 | 9/2002 | Forsell et al. |
| 5,863,366 | A | 1/1999 | Snow | 6,453,907 B1 | 9/2002 | Forsell et al. |
| 5,868,702 | A | 2/1999 | Stevens et al. | 6,454,698 B1 | 9/2002 | Forsell et al. |
| 5,873,837 | A | 2/1999 | Lieber et al. | 6,454,699 B1 | 9/2002 | Forsell et al. |
| 5,875,953 | A | 3/1999 | Shioya et al. | 6,454,700 B1 | 9/2002 | Forsell et al. |
| 5,879,499 | A | 3/1999 | Corvi | 6,454,701 B1 | 9/2002 | Forsell et al. |
| 5,881,919 | A | 3/1999 | Womac et al. | 6,461,292 B1 | 10/2002 | Forsell et al. |
| 5,885,238 | A | 3/1999 | Stevens et al. | 6,461,293 B1 | 10/2002 | Forsell et al. |
| 5,887,475 | A | 3/1999 | Muldner | 6,463,329 B1 | 10/2002 | Goedeke |
| 5,899,927 | A | 5/1999 | Ecker et al. | 6,463,935 B1 | 10/2002 | Forsell et al. |
| 5,916,179 | A | 6/1999 | Sharrock | 6,464,628 B1 | 10/2002 | Forsell et al. |
| 5,916,237 | A | 6/1999 | Schu | 6,470,212 B1 | 10/2002 | Weijand et al. |
| 5,935,078 | A | 8/1999 | Feierbach | 6,470,892 B1 | 10/2002 | Forsell et al. |
| 5,938,669 | A | 8/1999 | Klaiber et al. | 6,471,635 B1 | 10/2002 | Forsell et al. |
| 5,951,487 | A | 9/1999 | Brehmeier-Flick et al. | 6,475,136 B1 | 11/2002 | Forsell et al. |
| 5,957,861 | A | 9/1999 | Combs et al. | 6,475,170 B1 | 11/2002 | Doron et al. |
| 5,967,986 | A | 10/1999 | Cimochowski et al. | 6,482,145 B1 | 11/2002 | Forsell et al. |
| 5,971,934 | A | 10/1999 | Scherer et al. | 6,482,171 B1 | 11/2002 | Corvi et al. |
| 5,974,873 | A | 11/1999 | Nelson et al. | 6,482,177 B1 | 11/2002 | Leinders et al. |
| 5,978,985 | A | 11/1999 | Thurman | 6,486,588 B2 | 11/2002 | Doron et al. |
| 5,995,874 | A | 11/1999 | Borza et al. | 6,503,189 B1 | 1/2003 | Forsell et al. |
| 6,015,386 | A | 1/2000 | Kensey et al. | 6,504,286 B1 | 1/2003 | Porat et al. |
| 6,015,387 | A | 1/2000 | Schwartz et al. | 6,531,739 B2 | 3/2003 | Cable et al. |
| 6,019,729 | A | 2/2000 | Itoigawa et al. | 6,533,719 B2 | 3/2003 | Kuyava et al. |
| 6,024,704 | A | 2/2000 | Meador et al. | 6,533,733 B1 | 3/2003 | Ericson et al. |
| 6,030,413 | A | 2/2000 | Lazarus | 6,542,350 B1 | 4/2003 | Rogers |
| 6,033,366 | A | 3/2000 | Brockway et al. | 6,558,321 B1 | 5/2003 | Burd et al. |
| 6,035,461 | A | 3/2000 | Nguyen | 6,558,994 B2 | 5/2003 | Cha et al. |
| 6,053,873 | A | 4/2000 | Govari et al. | 6,573,563 B2 | 6/2003 | Lee et al. |
| 6,056,723 | A | 5/2000 | Donlon | 6,582,462 B1 | 6/2003 | Andersen et al. |
| 6,058,330 | A | 5/2000 | Borza et al. | 6,599,250 B2 | 7/2003 | Webb et al. |
| 6,059,757 | A | 5/2000 | Macoviak et al. | 6,605,112 B1 | 8/2003 | Moll et al. |
| 6,067,474 | A | 5/2000 | Schulman et al. | 6,629,534 B1 | 10/2003 | St. Goar et al. |
| 6,067,991 | A | 5/2000 | Forsell et al. | 6,640,137 B2 | 10/2003 | MacDonald |
| 6,076,016 | A | 6/2000 | Feierbach | 6,641,610 B2 | 11/2003 | Wolf et al. |
| 6,083,174 | A | 7/2000 | Brehmeier-Flick et al. | 6,645,143 B2 | 11/2003 | VanTassel et al. |
| 6,090,096 | A | 7/2000 | St. Goar et al. | 6,673,109 B2 | 1/2004 | Cox |
| 6,102,678 | A | 8/2000 | Peclat et al. | 6,678,561 B2 | 1/2004 | Forsell et al. |
| 6,102,856 | A | 8/2000 | Groff et al. | 6,682,480 B1 | 1/2004 | Habib et al. |
| 6,102,922 | A | 8/2000 | Jakobsson et al. | 6,682,503 B1 | 1/2004 | Fariss et al. |
| 6,106,477 | A | 8/2000 | Miesel et al. | 6,682,559 B2 | 1/2004 | Myers et al. |
| 6,106,551 | A | 8/2000 | Crossett et al. | 6,695,866 B1 | 2/2004 | Kuehn et al. |
| 6,110,145 | A | 8/2000 | Macoviak | 6,709,385 B2 | 3/2004 | Forsell et al. |
| 6,113,553 | A | 9/2000 | Chubbuck | 6,718,200 B2 | 4/2004 | Marmaropoulos et al. |
| 6,131,664 | A | 10/2000 | Sonnier | 6,719,787 B2 | 4/2004 | Cox |
| 6,135,945 | A | 10/2000 | Sultan | 6,719,788 B2 | 4/2004 | Cox |
| 6,159,156 | A | 12/2000 | Van Bockel et al. | 6,719,789 B2 | 4/2004 | Cox |
| 6,162,180 | A | 12/2000 | Miesel et al. | 6,731,976 B2 | 5/2004 | Penn et al. |
| 6,162,245 | A | 12/2000 | Jayaraman et al. | 6,733,525 B2 | 5/2004 | Yang et al. |
| 6,168,614 | B1 | 1/2001 | Andersen et al. | 6,736,846 B2 | 5/2004 | Cox |
| 6,234,745 | B1 | 5/2001 | Pugh et al. | 6,752,813 B2 | 6/2004 | Goldfarb et al. |
| 6,240,316 | B1 | 5/2001 | Richmond et al. | 6,796,942 B1 | 9/2004 | Kreiner et al. |
| 6,240,318 | B1 | 5/2001 | Phillips | 6,822,343 B2 | 11/2004 | Estevez |
| 6,245,102 | B1 | 6/2001 | Jayaraman | 6,851,628 B1 | 2/2005 | Garrison et al. |
| 6,248,080 | B1 | 6/2001 | Miesel et al. | 6,855,115 B2 | 2/2005 | Fonseca et al. |
| 6,251,093 | B1 | 6/2001 | Valley et al. | 6,889,772 B2 | 5/2005 | Buytaert et al. |
| 6,269,819 | B1 | 8/2001 | Oz et al. | 6,890,300 B2 | 5/2005 | Lloyd et al. |
| 6,277,078 | B1 | 8/2001 | Porat et al. | 6,896,651 B2 | 5/2005 | Gross et al. |
| 6,292,697 | B1 | 9/2001 | Roberts | 6,896,690 B1 | 5/2005 | Lambrecht et al. |
| 6,309,350 | B1 | 10/2001 | VanTassel et al. | 6,913,600 B2 | 7/2005 | Valley et al. |
| 6,315,769 | B1 | 11/2001 | Peer et al. | 6,915,165 B2 | 7/2005 | Forsell et al. |
| 6,319,208 | B1 | 11/2001 | Abita et al. | 6,926,246 B2 | 8/2005 | Ginggen et al. |
| 6,328,699 | B1 | 12/2001 | Eigler et al. | 6,929,653 B2 | 8/2005 | Strecter |
| 6,338,735 | B1 | 1/2002 | Stevens | 6,932,792 B1 | 8/2005 | St. Goar et al. |
| 6,357,438 | B1 | 3/2002 | Hansen | 6,951,229 B2 | 10/2005 | Garrison et al. |
| 6,360,122 | B1 | 3/2002 | Fischell et al. | 6,951,571 B1 | 10/2005 | Srivastava |
| 6,360,822 | B1 | 3/2002 | Robertson et al. | 6,953,429 B2 | 10/2005 | Forsell et al. |

| | | |
|---|---|---|
| 6,961,619 B2 | 11/2005 | Casey |
| 6,970,742 B2 | 11/2005 | Mann et al. |
| 6,979,350 B2 | 12/2005 | Moll et al. |
| 6,985,078 B2 | 1/2006 | Suzuki et al. |
| 6,989,027 B2 | 1/2006 | Allen et al. |
| 7,011,095 B2 | 3/2006 | Wolf et al. |
| 7,011,624 B2 | 3/2006 | Forsell et al. |
| 7,017,583 B2 | 3/2006 | Forsell et al. |
| 7,018,406 B2 | 3/2006 | Seguin et al. |
| 7,021,402 B2 | 4/2006 | Beato et al. |
| 7,025,727 B2 | 4/2006 | Brockway et al. |
| 7,044,920 B2 | 5/2006 | Letort et al. |
| 7,060,080 B2 | 6/2006 | Bachmann et al. |
| 7,081,683 B2 | 7/2006 | Ariav et al. |
| 7,109,933 B2 | 9/2006 | Ito et al. |
| 7,131,447 B2 | 11/2006 | Sterman et al. |
| 7,131,945 B2 | 11/2006 | Fink et al. |
| 7,134,580 B2 | 11/2006 | Garrison et al. |
| 7,144,400 B2 | 12/2006 | Byrum et al. |
| 7,147,640 B2 | 12/2006 | Huebner et al. |
| 7,153,262 B2 | 12/2006 | Stivoric et al. |
| 7,187,978 B2 | 3/2007 | Malek et al. |
| 7,225,032 B2 | 5/2007 | Schmeling et al. |
| 7,257,438 B2 | 8/2007 | Kinast |
| 7,285,090 B2 | 10/2007 | Stivoric et al. |
| 2001/0011543 A1 | 8/2001 | Forsell |
| 2001/0041823 A1 | 11/2001 | Snyder et al. |
| 2002/0049394 A1 | 4/2002 | Roy et al. |
| 2002/0120200 A1 | 8/2002 | Brockway et al. |
| 2002/0138009 A1 | 9/2002 | Brockway et al. |
| 2002/0177782 A1 | 11/2002 | Penner |
| 2003/0009201 A1 | 1/2003 | Forsell |
| 2003/0030893 A1 | 2/2003 | Cornelius et al. |
| 2003/0032857 A1 | 2/2003 | Forsell |
| 2003/0037591 A1 | 2/2003 | Ashton et al. |
| 2003/0045775 A1 | 3/2003 | Forsell |
| 2003/0066536 A1 | 4/2003 | Forsell |
| 2003/0088148 A1 | 5/2003 | Forsell |
| 2003/0092962 A1 | 5/2003 | Forsell |
| 2003/0093117 A1 | 5/2003 | Saadat |
| 2003/0100929 A1 | 5/2003 | Forsell |
| 2003/0105385 A1 | 6/2003 | Forsell |
| 2003/0109771 A1 | 6/2003 | Forsell |
| 2003/0114729 A1 | 6/2003 | Forsell |
| 2003/0125605 A1 | 7/2003 | Forsell |
| 2003/0125768 A1 | 7/2003 | Peter |
| 2003/0135089 A1 | 7/2003 | Forsell |
| 2003/0135090 A1 | 7/2003 | Forsell |
| 2003/0136417 A1 | 7/2003 | Fonseca et al. |
| 2003/0144648 A1 | 7/2003 | Forsell |
| 2003/0163079 A1 | 8/2003 | Burnett |
| 2003/0216666 A1 | 11/2003 | Ericson et al. |
| 2004/0054352 A1 | 3/2004 | Adams et al. |
| 2004/0113790 A1 | 6/2004 | Hamel et al. |
| 2004/0133092 A1 | 7/2004 | Kain |
| 2004/0147969 A1 | 7/2004 | Mann et al. |
| 2004/0172087 A1 | 9/2004 | Forsell |
| 2004/0186396 A1 | 9/2004 | Roy et al. |
| 2004/0254537 A1 | 12/2004 | Conlon et al. |
| 2005/0015014 A1 | 1/2005 | Fonseca et al. |
| 2005/0025979 A1 | 2/2005 | Sandt et al. |
| 2005/0027175 A1 | 2/2005 | Yang |
| 2005/0038328 A1 | 2/2005 | Stoehrer et al. |
| 2005/0061079 A1 | 3/2005 | Schulman |
| 2005/0102026 A1 | 5/2005 | Turner et al. |
| 2005/0159789 A1 | 7/2005 | Brockway et al. |
| 2005/0165317 A1 | 7/2005 | Turner et al. |
| 2005/0182330 A1 | 8/2005 | Brockway et al. |
| 2005/0187482 A1 | 8/2005 | O'Brien et al. |
| 2005/0187488 A1 | 8/2005 | Wolf |
| 2005/0192642 A1 | 9/2005 | Forsell |
| 2005/0240155 A1 | 10/2005 | Conlon |
| 2005/0240156 A1 | 10/2005 | Conlon |
| 2005/0250979 A1 | 11/2005 | Coe |
| 2005/0267406 A1 | 12/2005 | Hassler |
| 2005/0267500 A1 | 12/2005 | Hassler et al. |
| 2005/0272968 A1 | 12/2005 | Byrum et al. |
| 2005/0277960 A1 | 12/2005 | Hassler et al. |
| 2005/0277974 A1 | 12/2005 | Hassler et al. |
| 2005/0288604 A1 | 12/2005 | Eigler et al. |
| 2005/0288720 A1 | 12/2005 | Ross et al. |
| 2005/0288721 A1 | 12/2005 | Girouard et al. |
| 2005/0288739 A1 | 12/2005 | Hassler et al. |
| 2005/0288740 A1 | 12/2005 | Hassler et al. |
| 2005/0288741 A1 | 12/2005 | Hassler et al. |
| 2005/0288742 A1 | 12/2005 | Giordano et al. |
| 2006/0002035 A1 | 1/2006 | Gao et al. |
| 2006/0010090 A1 | 1/2006 | Brockway et al. |
| 2006/0020224 A1 | 1/2006 | Geiger |
| 2006/0020305 A1 | 1/2006 | Desai et al. |
| 2006/0035446 A1 | 2/2006 | Chang et al. |
| 2006/0047205 A1 | 3/2006 | Ludomirsky et al. |
| 2006/0049714 A1 | 3/2006 | Liu et al. |
| 2006/0058627 A1 | 3/2006 | Flaherty et al. |
| 2006/0064134 A1 | 3/2006 | Mazar et al. |
| 2006/0085051 A1 | 4/2006 | Fritsch |
| 2006/0089571 A1 | 4/2006 | Gertner |
| 2006/0094966 A1 | 5/2006 | Brockway et al. |
| 2006/0100531 A1 | 5/2006 | Moser |
| 2006/0113187 A1 | 6/2006 | Deng et al. |
| 2006/0122285 A1 | 6/2006 | Falloon et al. |
| 2006/0122863 A1 | 6/2006 | Gottesman et al. |
| 2006/0142635 A1 | 6/2006 | Forsell |
| 2006/0149124 A1 | 7/2006 | Forsell |
| 2006/0149324 A1 | 7/2006 | Mann et al. |
| 2006/0149327 A1 | 7/2006 | Hedberg et al. |
| 2006/0157701 A1 | 7/2006 | Bauer et al. |
| 2006/0161186 A1 | 7/2006 | Hassler et al. |
| 2006/0178617 A1 | 8/2006 | Adams et al. |
| 2006/0178695 A1 | 8/2006 | Decant et al. |
| 2006/0183967 A1 | 8/2006 | Lechner |
| 2006/0184206 A1 | 8/2006 | Baker et al. |
| 2006/0189887 A1 | 8/2006 | Hassler et al. |
| 2006/0189888 A1 | 8/2006 | Hassler et al. |
| 2006/0189889 A1 | 8/2006 | Gertner |
| 2006/0199997 A1 | 9/2006 | Hassler et al. |
| 2006/0211912 A1 | 9/2006 | Dlugos et al. |
| 2006/0211913 A1 | 9/2006 | Dlugos et al. |
| 2006/0211914 A1 | 9/2006 | Hassler et al. |
| 2006/0217668 A1 | 9/2006 | Schulze et al. |
| 2006/0217673 A1 | 9/2006 | Schulze et al. |
| 2006/0235310 A1 | 10/2006 | O'Brien et al. |
| 2006/0235439 A1 | 10/2006 | Molitor et al. |
| 2006/0235448 A1 | 10/2006 | Roslin et al. |
| 2006/0244914 A1 | 11/2006 | Cech et al. |
| 2006/0247682 A1 | 11/2006 | Gerber et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0247723 A1 | 11/2006 | Gerber et al. |
| 2006/0247724 A1 | 11/2006 | Gerber et al. |
| 2006/0247725 A1 | 11/2006 | Gerber et al. |
| 2006/0252982 A1 | 11/2006 | Hassler et al. |
| 2006/0293625 A1 | 12/2006 | Hunt et al. |
| 2006/0293626 A1 | 12/2006 | Byrum et al. |
| 2006/0293627 A1 | 12/2006 | Byrum et al. |
| 2007/0010790 A1 | 1/2007 | Byrum et al. |
| 2007/0027356 A1 | 2/2007 | Ortiz |
| 2007/0027493 A1 | 2/2007 | Ben-Haim et al. |
| 2007/0067206 A1 | 3/2007 | Haggerty et al. |
| 2007/0070906 A1 | 3/2007 | Thakur |
| 2007/0072452 A1 | 3/2007 | Inagaki et al. |
| 2007/0081304 A1 | 4/2007 | Takeguchi |
| 2007/0156013 A1 | 7/2007 | Birk |
| 2007/0161958 A1 | 7/2007 | Glenn |
| 2007/0167672 A1 | 7/2007 | Dlugos et al. |
| 2007/0167988 A1* | 7/2007 | Cernasov ................... 607/35 |
| 2007/0173881 A1 | 7/2007 | Birk et al. |
| 2007/0179583 A1 | 8/2007 | Goetzinger et al. |
| 2007/0208313 A1 | 9/2007 | Conlon et al. |
| 2007/0225781 A1 | 9/2007 | Saadat et al. |
| 2007/0265645 A1 | 11/2007 | Birk et al. |
| 2007/0299296 A1* | 12/2007 | Vaska ........................ 600/16 |
| 2008/0009680 A1 | 1/2008 | Hassler |
| 2009/0171379 A1 | 7/2009 | Coe et al. |

FOREIGN PATENT DOCUMENTS

| | | |
|---|---|---|
| CA | 1119469 | 3/1982 |
| CA | 1275135 | 10/1990 |
| CA | 1277885 | 12/1990 |
| CA | 1317482 | 5/1993 |
| CA | 2082015 | 5/1993 |
| CA | 1327191 | 2/1994 |
| CA | 2119101 | 9/1994 |
| CA | 2305998 | 4/1999 |
| CN | 1059035 | 2/1992 |
| CN | 1119469 | 3/1996 |
| CN | 1241003 | 1/2000 |
| CN | 1739467 A | 3/2006 |
| EA | 4581 | 6/2004 |
| EP | 125387 B1 | 11/1984 |
| EP | 417171 | 3/1991 |
| EP | 508141 | 10/1992 |
| EP | 568730 | 11/1993 |
| EP | 605302 | 7/1994 |
| EP | 660482 | 6/1995 |
| EP | 714017 | 5/1996 |
| EP | 769340 | 4/1997 |
| EP | 846475 | 6/1998 |
| EP | 848780 | 6/1998 |
| EP | 876808 | 11/1998 |
| EP | 888079 | 1/1999 |
| EP | 914059 | 5/1999 |
| EP | 0941712 A1 | 9/1999 |
| EP | 981293 | 3/2000 |
| EP | 997680 | 5/2000 |
| EP | 1003021 | 5/2000 |
| EP | 1022983 | 8/2000 |
| EP | 1050265 | 11/2000 |
| EP | 1115329 | 7/2001 |
| EP | 1119314 | 8/2001 |
| EP | 1128871 | 9/2001 |
| EP | 1202674 | 5/2002 |
| EP | 1213991 | 6/2002 |
| EP | 1253877 | 11/2002 |
| EP | 1253879 | 11/2002 |
| EP | 1253880 | 11/2002 |
| EP | 1253881 | 11/2002 |
| EP | 1253883 | 11/2002 |
| EP | 1253888 | 11/2002 |
| EP | 1255511 | 11/2002 |
| EP | 1255513 | 11/2002 |
| EP | 1255514 | 11/2002 |
| EP | 1263355 | 12/2002 |
| EP | 1263357 | 12/2002 |
| EP | 1284691 | 2/2003 |
| EP | 1374758 | 1/2004 |
| EP | 1488735 | 12/2004 |
| EP | 1500411 | 1/2005 |
| EP | 1510306 | 3/2005 |
| EP | 1518514 | 3/2005 |
| EP | 1545303 | 6/2005 |
| EP | 1547549 | 6/2005 |
| EP | 1563814 | 8/2005 |
| EP | 1568338 | 8/2005 |
| EP | 1582175 | 10/2005 |
| EP | 1582176 | 10/2005 |
| EP | 1584303 | 10/2005 |
| EP | 1586283 | 10/2005 |
| EP | 1591086 | 11/2005 |
| EP | 1593359 | 11/2005 |
| EP | 1598030 | 11/2005 |
| EP | 1609440 | 12/2005 |
| EP | 1674033 | 6/2006 |
| EP | 1736123 | 12/2006 |
| EP | 1799119 | 6/2007 |
| EP | 1815881 A1 | 8/2007 |
| EP | 1832252 A2 | 9/2007 |
| FR | 2730158 A1 | 8/1996 |
| GB | 2355937 | 5/2001 |
| WO | WO-8911244 | 11/1989 |
| WO | WO-8911701 | 11/1989 |
| WO | WO-9004368 | 5/1990 |
| WO | WO-9511057 | 4/1995 |
| WO | WO-9715351 | 5/1997 |
| WO | WO-9733513 | 9/1997 |
| WO | WO-9833554 | 8/1998 |
| WO | WO-9835610 | 8/1998 |
| WO | WO-9901063 | 1/1999 |
| WO | WO-9918850 | 4/1999 |
| WO | WO-0004945 | 2/2000 |
| WO | WO-0009047 A1 | 2/2000 |
| WO | WO-0033738 | 6/2000 |
| WO | WO-0072899 | 12/2000 |
| WO | WO-0104487 | 1/2001 |
| WO | WO-0108597 A1 | 2/2001 |
| WO | WO-0112075 | 2/2001 |
| WO | WO-0112076 | 2/2001 |
| WO | WO-0112077 | 2/2001 |
| WO | WO-0112078 | 2/2001 |
| WO | WO-0121066 | 3/2001 |
| WO | WO-0136014 | 5/2001 |
| WO | WO-0145485 | 6/2001 |
| WO | WO-0145486 | 6/2001 |
| WO | WO-0147431 | 7/2001 |
| WO | WO-0147432 | 7/2001 |
| WO | WO-0147433 | 7/2001 |
| WO | WO-0147434 | 7/2001 |
| WO | WO-0147435 | 7/2001 |
| WO | WO-0147440 | 7/2001 |
| WO | WO-0147575 | 7/2001 |
| WO | WO-0147575 A2 | 7/2001 |
| WO | WO-0148451 | 7/2001 |
| WO | WO-0149245 | 7/2001 |
| WO | WO-0150832 | 7/2001 |
| WO | WO-0150833 | 7/2001 |
| WO | WO-0154626 | 8/2001 |
| WO | WO-0158388 | 8/2001 |
| WO | WO-0158390 | 8/2001 |
| WO | WO-0158391 | 8/2001 |
| WO | WO-0158393 | 8/2001 |
| WO | WO-0160453 | 8/2001 |
| WO | WO-0181890 | 11/2001 |
| WO | WO-0200118 | 1/2002 |
| WO | WO-0215769 | 2/2002 |
| WO | WO-0226161 | 4/2002 |
| WO | WO-02053228 | 7/2002 |
| WO | WO-02055126 | 7/2002 |
| WO | WO-02058551 | 8/2002 |
| WO | WO-02065894 | 8/2002 |
| WO | WO-02076289 | 10/2002 |
| WO | WO-02082984 | 10/2002 |
| WO | WO-02089655 | 11/2002 |
| WO | WO-02090894 | 11/2002 |
| WO | WO-02100481 | 12/2002 |
| WO | WO-03002192 | 1/2003 |
| WO | WO-03002193 | 1/2003 |
| WO | WO-03020182 | 3/2003 |
| WO | WO-03061467 | 7/2003 |
| WO | WO-03061504 | 7/2003 |
| WO | WO-03096889 | 11/2003 |
| WO | WO-2004014245 A1 | 2/2004 |
| WO | WO-2004014456 | 2/2004 |
| WO | WO-2004019773 | 3/2004 |
| WO | WO-2004058101 | 7/2004 |
| WO | WO-2004066879 | 8/2004 |
| WO | WO-2004110263 | 12/2004 |
| WO | WO-2005000206 | 1/2005 |
| WO | WO-2005007075 | 1/2005 |
| WO | WO-2005107583 | 11/2005 |
| WO | WO-2006001851 | 1/2006 |
| WO | WO-2006035446 | 4/2006 |
| WO | WO-2006108203 A2 | 10/2006 |
| WO | WO-2006113187 | 10/2006 |
| WO | WO-2006118790 A2 | 11/2006 |
| WO | WO-2006122285 | 11/2006 |
| WO | WO-2007067206 | 6/2007 |
| WO | WO-2007070906 | 6/2007 |
| WO | WO-2007072452 | 6/2007 |
| WO | WO-2007081304 | 7/2007 |
| WO | WO-2007104356 | 9/2007 |

OTHER PUBLICATIONS

European Search Report, Application No. 08254160.8, Issued Jul. 28, 2009, 11 pages.

"Application Specific Integrated Circuits (ASICs)", Honeywell product information from website http://www.honeywell.com/sites/portal?smap=aerospace&page=Radiation-Hardened-Electronics3&theme=T18&catID=CE06BEF88-65F8-6A1E-4ED1-6A1EC1B7AE7A&id=HA0E380D3-C27B-9EBF-AAC8-9FAF8851256D&sel=1&sel4=1; 1 page.

"Rad Hard Aerospace Components Products", Honeywell product and service information from website http://www.honeywell.com/sites/portal?smap=aerospace&page=Radiation-Hardened-Electronics3&theme=T6&catID=C815147E4-8786-29FE-49EB-C21C8790AA99&id=H0166BA51-5344-E57E-5C37-C6333EA43F61&sel=1; 1 page.

"Radiation Hardened Electronics and Radiation Technology", Honeywell product and service information from website http://www.honeywell.com/sites/portal?smap=aerospace&page=Radiation-Hardened-Electronics&theme=T4; 2 pages.

Kirchner, G., "Honeywell and Synopsys: Concept-to-Parts Solutions for Next Generation Rad-Hard ASICs", in online magazine Compiler, http://www.synopsys.com/news/pubs/compiler/artlead_redasic-apr05.html, Apr. 2005, 5 pages.

P.A. Neukomm and H. Kundig, "Passive Wireless Actuator Control and Sensor Signal Transmission," Sensors and Actuators, A21-A23 (1990) 258-262.

Chinese Office Action, Applicaton No. 200810189316.4, mailed Jul. 14, 2011, 2 pages.

European Search Report, Application No. 08254160.8, Issued Nov. 19, 2010, 4 pages.

* cited by examiner

CONTROLLING PRESSURE IN ADJUSTABLE RESTRICTION DEVICES

FIELD OF THE INVENTION

The present invention relates to implantable restriction devices, and in particular to methods and devices for transient pressure control of fluid in a restriction system.

BACKGROUND OF THE INVENTION

Obesity is becoming a growing concern, particularly in the United States, as the number of obese people continues to increase, and more is learned about the negative health effects of obesity. Morbid obesity, in which a person is 100 pounds or more over ideal body weight, in particular poses significant risks for severe health problems. Accordingly, a great deal of attention is being focused on treating obese patients. One method of treating morbid obesity has been to place a restriction device, such as an elongated band, about the upper portion of the stomach. Gastric bands have typically comprised a fluid-filled elastomeric balloon with fixed endpoints that encircles the stomach just inferior to the esophageal-gastric junction to form a small gastric pouch above the band and a reduced stoma opening in the stomach. When fluid is infused into the balloon, the band expands against the stomach creating a food intake restriction or stoma in the stomach. To decrease this restriction, fluid is removed from the band. The effect of the band is to reduce the available stomach volume and thus the amount of food that can be consumed before becoming "full."

With each of the above-described food restriction devices, safe, effective treatment requires that the device be regularly monitored and adjusted to vary the degree of restriction applied to the stomach. With banding devices, the gastric pouch above the band will substantially increase in size following the initial implantation. Accordingly, the stoma opening in the stomach must initially be made large enough to enable the patient to receive adequate nutrition while the stomach adapts to the banding device. As the gastric pouch increases in size, the band may be adjusted to vary the stoma size. In addition, it is desirable to vary the stoma size in order to accommodate changes in the patient's body or treatment regime, or in a more urgent case, to relieve an obstruction or severe esophageal dilatation. Traditionally, adjusting a hydraulic gastric band requires a scheduled clinician visit during which a hypodermic needle and syringe are used to permeate the patient's skin and add or remove fluid from the balloon. More recently, implantable pumps have been developed which enable non-invasive adjustments of the band. An external programmer communicates with the implanted pump using telemetry to control the pump. During a scheduled visit, a physician places a hand-held portion of the programmer near the gastric implant and transmits power and command signals to the implant. The implant in turn adjusts the fluid levels in the band and transmits a response command to the programmer. While such pumps can be effective, they require power to operate, requiring patients to visit physicians for the pumps to properly operate and be maintained.

Accordingly, there remains a need for methods and devices for regulating a hydraulic restriction system, and in particular for methods and devices that do not require the use of power to operate.

SUMMARY OF THE INVENTION

The present invention generally provides methods and devices for regulating a hydraulic restriction system. In one embodiment, a system for forming a restriction in a patient is provided that includes a restriction device that can form a restriction in a pathway, a pumping mechanism that can pump fluid between a fluid source and the restriction device, and an energy release mechanism coupled to the pumping mechanism. The energy release mechanism can release stored potential energy to activate the pumping mechanism to pump fluid between a fluid source and the restriction device, such as by using a gear-driven system. Pumping fluid into the restriction device can be effective to increase an amount of restriction formed by the restriction device. In some embodiments, the pumping mechanism can pump fluid in a single direction away from a fluid source and into the restriction device. Additionally, the pumping mechanism can be configured to allow release of fluid from the restriction device only when the energy release mechanism is not releasing stored potential energy to activate the pumping mechanism.

The system can have any number of variations. For example, the system can include an energy storage mechanism coupled to the energy release mechanism and that can store potential energy. In some embodiments, the system can also include an energy charging mechanism coupled to the energy storage mechanism and that can receive energy and transfer received energy to the energy storage mechanism. In some embodiments, the energy storage mechanism can receive energy converted from kinetic energy derived from movement of a patient having the energy charging mechanism implanted therein. The energy storage mechanism and the energy charging mechanism can be in fluid communication with one another such that energy can be released from the energy charging mechanism into the energy storage mechanism by transferring fluid from the energy charging mechanism into the energy storage mechanism. In some embodiments, the energy charging mechanism can receive fluid from a second fluid source not in fluid communication with the restriction device. In some embodiments, the energy charging mechanism can receive applied kinetic energy derived from movement of a patient having the energy charging mechanism implanted therein.

In another embodiment, a system for forming a restriction in a patient includes a restriction device that can form a restriction in a pathway and a flexible pump coupled to the restriction device and that can release fluid from a fluid source (e.g., an implanted fluid reservoir) into the restriction device when the flexible pump is manually activated. Adding fluid to the restriction device can increase an amount of restriction formed by the restriction device. The system can also include a valve (e.g., a check valve) coupled to the restriction device and that can open to allow fluid to flow out of the restriction device when a pressure of fluid in the restriction device is greater than a pre-set pressure limit, which can be fixed or adjustable. The valve can be optionally coupled to the fluid source and configured to open to allow fluid to flow out of the restriction device and into the fluid source. In some embodiments, the system includes a second valve coupled to the restriction device and having a locked position and that can open to allow fluid to flow from the restriction device and into the fluid source when manually released from the locked position, e.g., by moving an external device in proximity of an implanted location of the second valve.

The system can have any number of variations. For example, the flexible pump can be implanted beneath tissue and be manually activated through tissue. As another example, the flexible pump can be manually activated from within a patient in which the flexible pump is implanted through movement of the patient. In some embodiments, the system can include a valve coupled between the flexible pump and the restriction device and that can allow the flexible pump to pump fluid in a single direction from a fluid source and into the restriction device.

In other aspects, a method of forming a restriction in a patient is provided. The method can include applying energy to an energy charging mechanism that delivers the energy to an energy storage mechanism which stores the energy. The energy storage mechanism can release the stored energy to cause fluid to flow from a fluid source into a restriction device that is implanted to form a restriction in a pathway. Fluid flow from the fluid source into the restriction device can increase an amount of restriction applied to the pathway by the restriction device. In certain exemplary embodiments, the energy storage mechanism can release energy to an energy release mechanism that causes a pumping mechanism to pump fluid from the fluid source into the restriction device. In some embodiments, energy stored in the energy storage mechanism is released only when the energy charging mechanism is not delivering energy to the energy storage mechanism.

Energy can be applied to the energy charging mechanism in a variety of ways. For example, applying energy to the energy charging mechanism can include applying kinetic energy generated by movement of a patient having the restriction device implanted therein. As another example, applying energy to the energy charging mechanism can include placing a magnetic device in proximity to the energy charging mechanism.

In some embodiments, when energy is applied to the energy charging mechanism, fluid can be transferred from the energy charging mechanism into the energy storage mechanism to deliver the energy to the energy storage mechanism. Furthermore, when the energy storage mechanism releases the stored energy, fluid can be transferred from the energy storage mechanism to a fluid source.

In another embodiment, a method of forming a restriction in a patient includes pumping a subcutaneous flexible pump that is coupled to a restriction device that is implanted to form a restriction in a pathway to cause fluid to flow from a fluid source into the restriction device, in some embodiments in a single direction from the fluid source toward the restriction device. When a pressure of fluid in the restriction device is greater than a pre-set pressure limit of a valve coupled to the restriction device, the valve opens to allow fluid to flow out of the restriction device. The pre-set pressure limit can be fixed or adjustable. In some embodiments, fluid can flow out of the restriction device toward the fluid source when a second valve coupled to the restriction device is manually released from a locked position.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for regulating a hydraulic restriction system that is configured to form a restriction in a pathway. In general, the methods and devices can allow for non-invasive, transient pressure control using an implantable control mechanism. The methods and devices can also, in some embodiments, mechanically regulate pressure of the restriction device without using any electrical components that may need to be powered to operate over extended periods of time.

While the present invention can be used with a variety of restriction systems known in the art, in an exemplary embodiment the devices and methods are used with a gastric restriction device. While various types of gastric restriction devices are known, including electrical, mechanical, and/or fluid-based devices, for reference purposes the devices and methods disclosed herein are discussed in connection various embodiments of a fluid-based gastric restriction device as disclosed in commonly-owned U.S. Publication No. 2006/0211913 of Dlugos et al. (hereinafter "Dlugos") filed on Mar. 7, 2006 and entitled "Non-Invasive Pressure Measurement In A Fluid Adjustable Restrictive Device," which is hereby incorporated by reference in its entirety. A person skilled in the art will appreciate that the methods and devices disclosed herein are not intended to be limited to use with any particular restriction device.

Figure 1A:
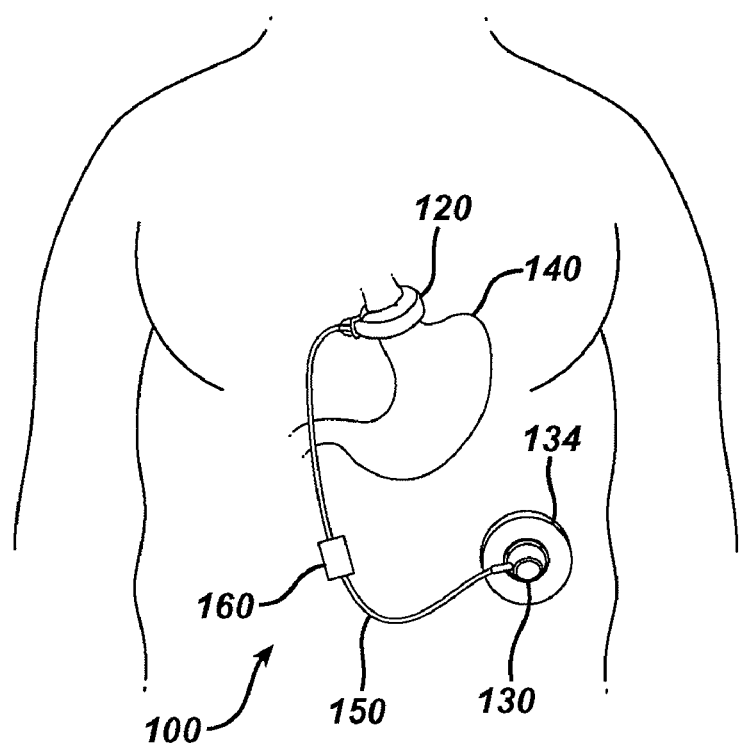
FIG. 1A is a schematic diagram of one embodiment of a food intake restriction system.
Figure 1B:
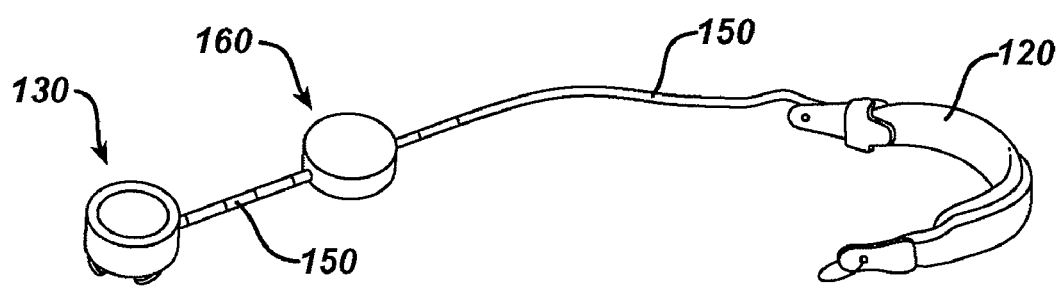
FIG. 1B is a perspective view of the food intake restriction system of FIG. 1A.

FIGS. 1A-1B illustrate one embodiment of an implantable restriction system 100, as disclosed in Dlugos. As shown, the implantable restriction system 100 generally includes an adjustable gastric band 120 that is configured to be positioned around the upper portion of a patient's stomach 140 and an injection port 130 that is fluidly coupled to the adjustable gastric band 120, e.g., via a catheter 150 (which can be formed from one or more components). The injection port 130 is adapted to allow fluid to be introduced into and removed from the gastric band 120 to thereby adjust the size of the band 120 and thus the pressure applied to the stomach 140. The injection port 130 can thus be implanted at a location within the body that is accessible through the tissue. Typically, injection ports are positioned in the lateral subcostal region of the patient's abdomen under the skin and layers of fatty tissue. Surgeons also typically implant injection ports on the sternum of the patient.

Figure 2A:
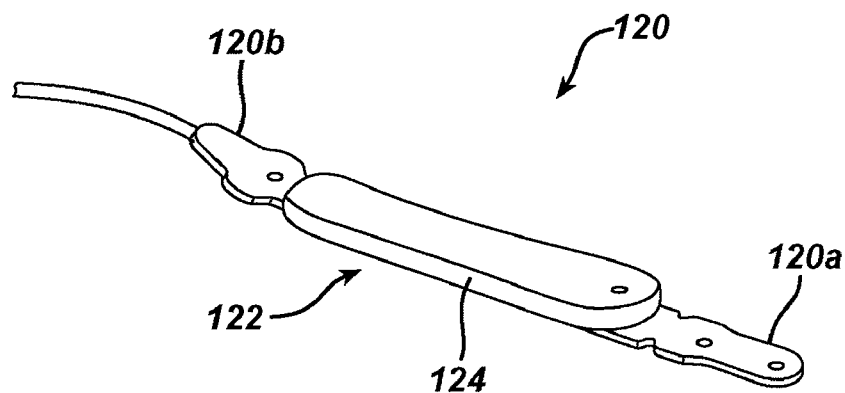
FIG. 2A is a perspective view of a gastric band of the food intake restriction device of FIG. 1A.

FIG. 2A shows the gastric band 120 in more detail. While the gastric band 120 can have a variety of configurations, and various gastric bands currently known in the art can be used with the present invention, in the illustrated embodiment the gastric band 120 has a generally elongate shape with a support structure 122 having first and second opposite ends 120a, 120b that can be formed in a loop such that the ends are secured to each other. Various mating techniques can be used to secure the ends 120a, 120b to one another. In the illustrated embodiment, the ends 120a, 120b are in the form of straps that mate together, with one laying on top of the other. A support structure can be included at one end of the gastric band 120, and it can have an opening through which the other end of the gastric band 120 can feed through to secure the ends to one another. The gastric band 120 can also include a variable volume member, such as an inflatable balloon 124, that is disposed or formed on an internal side of the support structure 122 and that is configured to be positioned adjacent to tissue. The balloon 124 can expand or contract against the outer wall of the stomach to form an adjustable stoma for controllably restricting food intake into the stomach. The balloon 124 can receive fluid to expand and release fluid to contract. An amount of fluid within the balloon can correspond to an amount of restriction created by the band 120. Thus, adjustment of fluid in the band 120 can be used to control the amount of restriction formed by the band 120.

A person skilled in the art will appreciate that the gastric band 120 can have a variety of other configurations. Moreover, the various methods and devices disclosed herein have equal applicability to other types of implantable bands. For example, bands are used for the treatment of fecal incontinence, as described in U.S. Pat. No. 6,461,292 which is hereby incorporated by reference in its entirety. Bands can also be used to treat urinary incontinence, as described in U.S. Publication No. 2003/0105385 which is hereby incorporated by reference in its entirety. Bands can also be used to treat heartburn and/or acid reflux, as disclosed in U.S. Pat. No. 6,470,892 which is hereby incorporated by reference in its entirety. Bands can also be used to treat impotence, as described in U.S. Publication No. 2003/0114729 which is hereby incorporated by reference in its entirety.

Figure 2B:
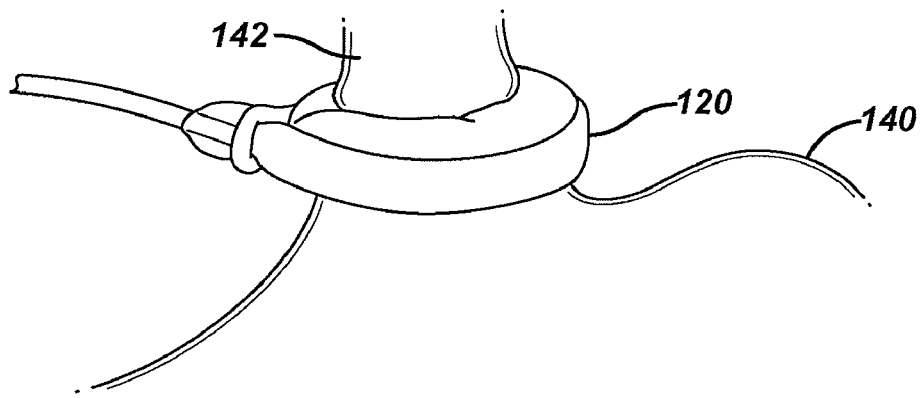
FIG. 2B is a schematic diagram of the gastric band of FIG. 2A applied about the gastro-esophageal junction of a patient.

FIG. 2B shows the adjustable gastric band 120 applied about the gastro-esophageal junction of a patient. As shown, the band 120 at least substantially encloses the upper portion of the stomach 140 near the junction with the patient's esophagus 142. After the band 120 is implanted, preferably in the deflated configuration wherein the band 120 contains little or no fluid, the band 120 can be inflated, e.g., using saline, to decrease the size of the stoma opening. A person skilled in the art will appreciate that various techniques, including those described below, can be used to adjust the amount of restriction formed by the band 120.

Figure 3:
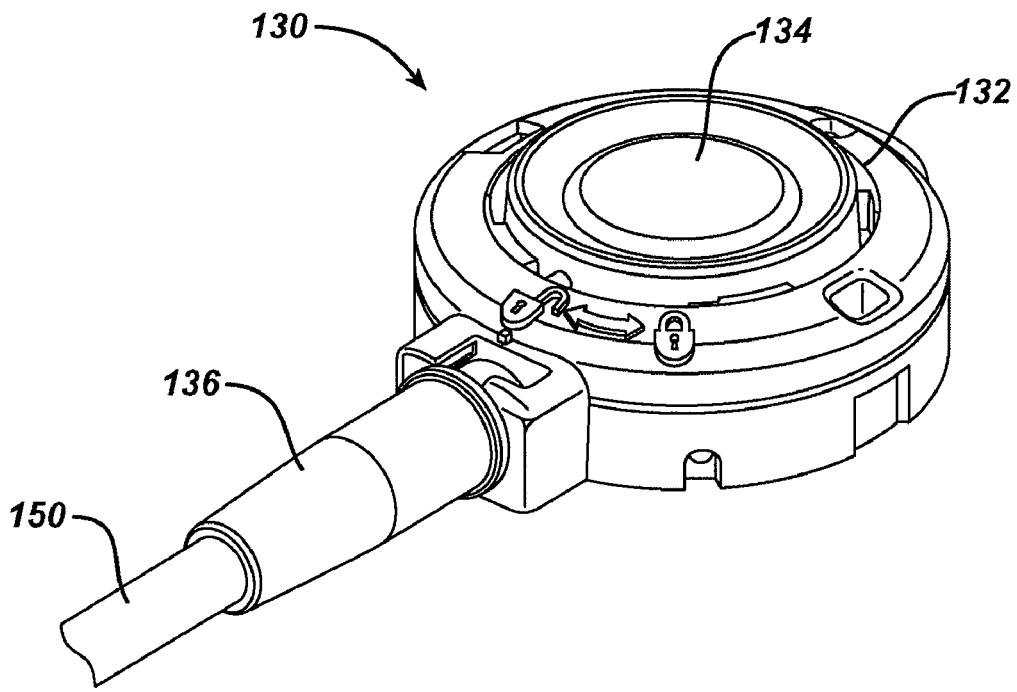
FIG. 3 is a perspective view of one embodiment of an injection port housing of the food intake restriction system of FIG. 1A.

The fluid injection port 130 can also have a variety of configurations, and it can optionally be provided to allow fluid or other materials to be introduced into various components of the system 100, such as the band 120, a transient pressure control mechanism 160 as will be discussed in more detail below, and/or one or more fluid sources. The port 130 can have a variety of configurations. In the embodiment shown in FIG. 3, the injection port 130 has a generally cylindrical housing with a distal or bottom surface and a perimeter wall extending proximally from the bottom surface and defining a proximal opening 132. The proximal opening 132 can include a needle-penetrable septum 134 extending there across and providing access to a fluid source or reservoir (not visible in FIG. 3) formed within the housing. The septum 134 is preferably placed in a proximal enough position such that the depth of the reservoir is sufficient enough to expose the open tip of a needle, such as a Huber needle, so that fluid transfer can take place. The septum 134 is preferably arranged so that it will self seal after being punctured by a needle and the needle is withdrawn. As further shown in FIG. 3, the port 130 can further include a catheter tube connection member 136 that is in fluid communication with the reservoir and that is configured to couple to a catheter (e.g., the catheter 150). A person skilled in the art will appreciate that the housing can be made from any number of materials, typically biocompatible materials such as stainless steel, titanium, or polymeric materials, and the septum 134 can likewise be made from any number of materials, typically biocompatible materials, including silicone. Moreover, the system also may not have an injection port 130. Various configurations are possible, and any known restriction system or device can be used with the present invention.

The illustrated system 100 also includes the control mechanism 160 disposed in-line with the gastric band 120 and a fluid source, which, as further discussed below, can be included in the injection port 130 or can be located elsewhere within the system 100. Although the control mechanism 160 can be disposed anywhere to allow fluid delivery to the band 120, in the illustrated embodiment the catheter 150 includes a first portion that is coupled between the gastric band 120 and the control mechanism 160 and a second portion that is coupled between the control mechanism 160 and the injection port 130. As explained further below, the control mechanism 160 can controllably release fluid from a fluid source into the band 120 to help maintain a desirable pressure of fluid in the band 120. In this way, the control mechanism 160 can allow for non-invasive pressure control. The control mechanism 160 can also, in an exemplary embodiment, mechanically regulate pressure of the band 120 without using any electrical components that may need to be powered to operate over extended periods of time.

The illustrated system 100 can also optionally include a sensor such as a pressure reading device 134 for reading the pressure of the fluid within the closed fluid circuit of the system 100. The pressure reading device 134, however, need not be included in the system 100 and is merely shown as an optional feature. While Dlugos discloses a pressure reading device 134, the device could be any sensing device for sensing various parameters of the system 100 or external to the system 100. The sensing device can also have various configurations, and it can be coupled to or positioned anywhere in the restriction system 100. In the illustrated embodiment in FIG. 1A, the pressure reading device 134 is coupled to the injection port 130. In addition to sensing the pressure of fluid in the closed system, a pressure of fluid within the esophagus, the stomach 140, or other body lumen can also be sensed using any suitable device, such as an endoscopic manometer. By way of non-limiting example, such fluid pressure measurements can be compared against the measured pressure of fluid within the system 100 before, during, and/or after adjustment of pressure within the system 100. Other suitable uses for measured pressure within the esophagus, the stomach 140, or other body lumen will be appreciated by those skilled in the art. The sensor can also be configured to measure various other physiological parameters, as may be desired. FIG. 2B shows an alternate location of a sensing device, disposed in a buckle of the band 120.

Figure 4:
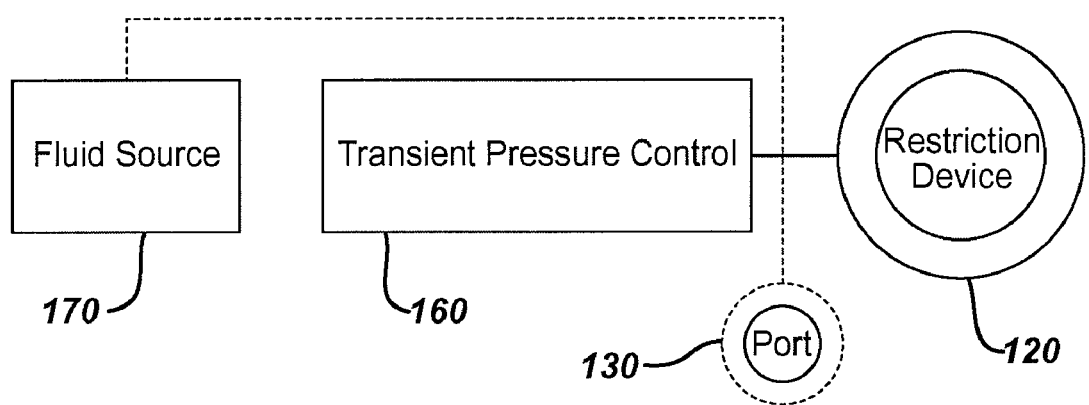
FIG. 4 is a block diagram a food intake restriction system having a transient pressure control system.

As mentioned above and as illustrated in FIG. 4, the control mechanism 160 can be disposed in-line with the band 120 and a fluid source 170. The fluid source 170 can have various configurations, and the system 100 can include any number of fluid sources. For example, the fluid source 170 can be in the form of a rigid or flexible housing coupled to the control mechanism 160 by a catheter (e.g., the catheter 150) or other connector. As another example, the fluid source 170 can be the human body (e.g., the stomach, peritoneum, lung, saline generated through osmosis, intracellular fluids, blood, etc.). A catheter or other pathway can extend from the control mechanism 160 to a location in the body where it is desirable to obtain and/or release fluid. As indicated above, the fluid source 170 can also or alternatively be included in the port 130. The port 130 is thus shown in dotted outline form in FIG. 4 because in some embodiments, the fluid source 170 and the port 130 can be part of the same housing, in which case the fluid source 170 of FIG. 4 would also represent the port 130. Additionally, if the fluid source 170 is not disposed in the port 130, it may or may not be in fluid communication with the port 130 through a catheter (e.g., the catheter 150) or other connector.

Figure 5:
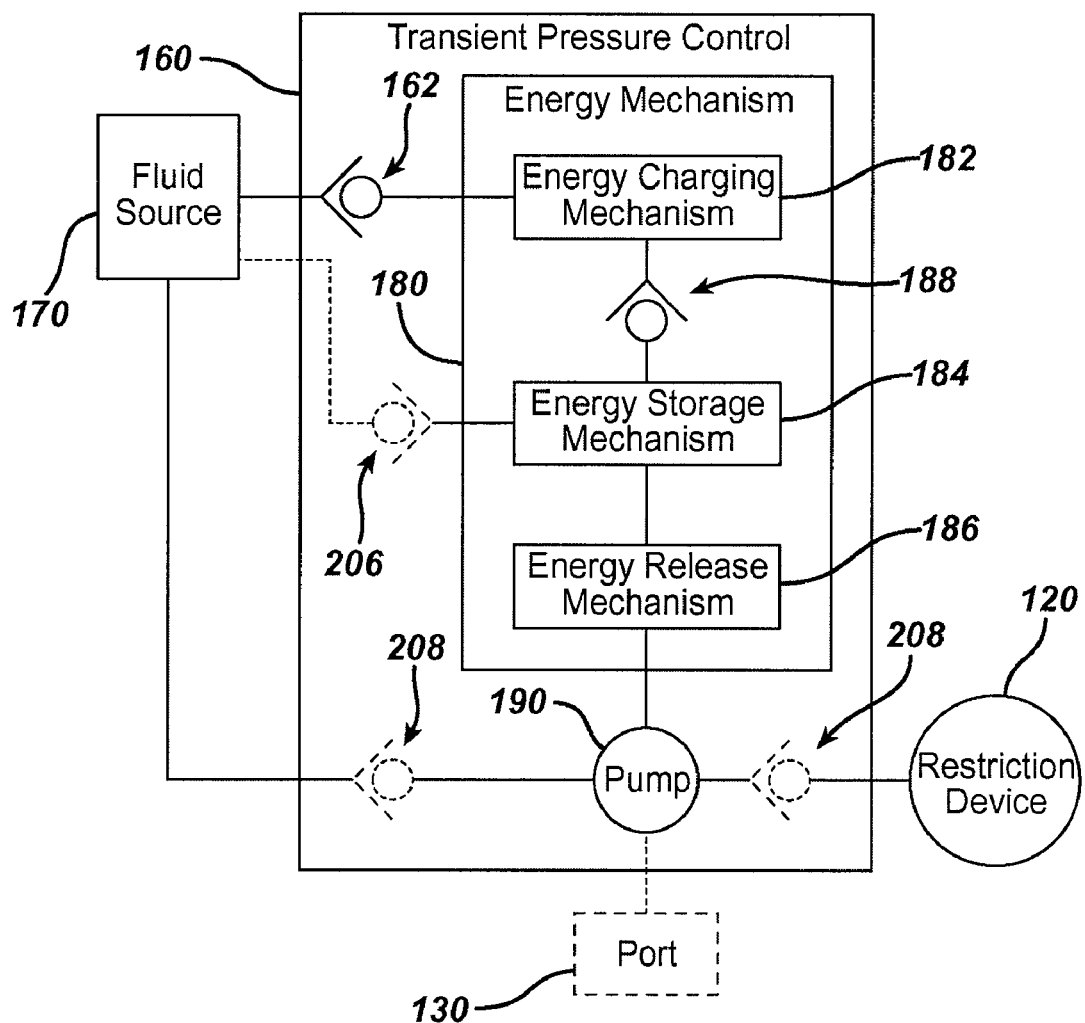
FIG. 5 is a block diagram of one exemplary embodiment of a transient pressure control system.

Various control mechanisms can be used to control the pressure of fluid in the band 120. The control mechanism 160 (including each of the elements within it) can have any configuration, size, and shape and can be made from any type of and any combination of materials, typically biocompatible materials appropriate for use in a body, such as a polymer, biocompatible metal, and other similar types of materials. In an exemplary embodiment, the control mechanism 160 can be mechanical and non-electrical, such that power is not required. In use, the control mechanism 160 can be configured to receive energy, e.g., via subcutaneous pumping, inertial pumping, or mechanical pumping, and to use that energy to adjust the pressure of the band 120. In an exemplary embodiment, the control mechanism 160 maintains the pressure within a range, with the upper limit of the range being pre-set (fixed or adjustable by a user), and the lower limit of the range being defined by the decrease of forces generated by tissue proximate to the band 120, as observed in the restriction system, e.g., as the patient loses weight, etc. In certain exemplary embodiments, the upper limit can be maintained by the control mechanism and optionally by allowing the release of fluid in a low pressure portion of the fluid circuit or into the body. FIG. 5 illustrates one exemplary embodiment of a control mechanism 160. As shown, the control mechanism 160 includes an energy mechanism 180 and a pumping mechanism (e.g., a pump 190). Generally, in use, energy can be applied to the energy mechanism 180, which can store the energy. The energy mechanism 180 can release stored energy to activate the pump 190, thereby causing fluid to flow from the fluid source 170 into the band 120.

The energy mechanism 180 can have various configurations, but in an exemplary embodiment it includes an energy charging mechanism 182 coupled to the fluid source 170, an energy storage mechanism 184 coupled to the energy charging mechanism 182 (and optionally to the fluid source 170), and an energy release mechanism 186 coupled to the energy storage mechanism 184. The pump 190 can be coupled to the energy release mechanism 186. One or more of the elements included in the energy mechanism 180 can be combined together in any combination. For example, the energy charging mechanism 182 and the energy storage mechanism 184 can include a single housing configured to receive applied energy and to store the received energy. The energy charging mechanism 182 can receive energy input to the energy mechanism 180 and transfer received energy to the energy storage mechanism 186.

Figure 6:
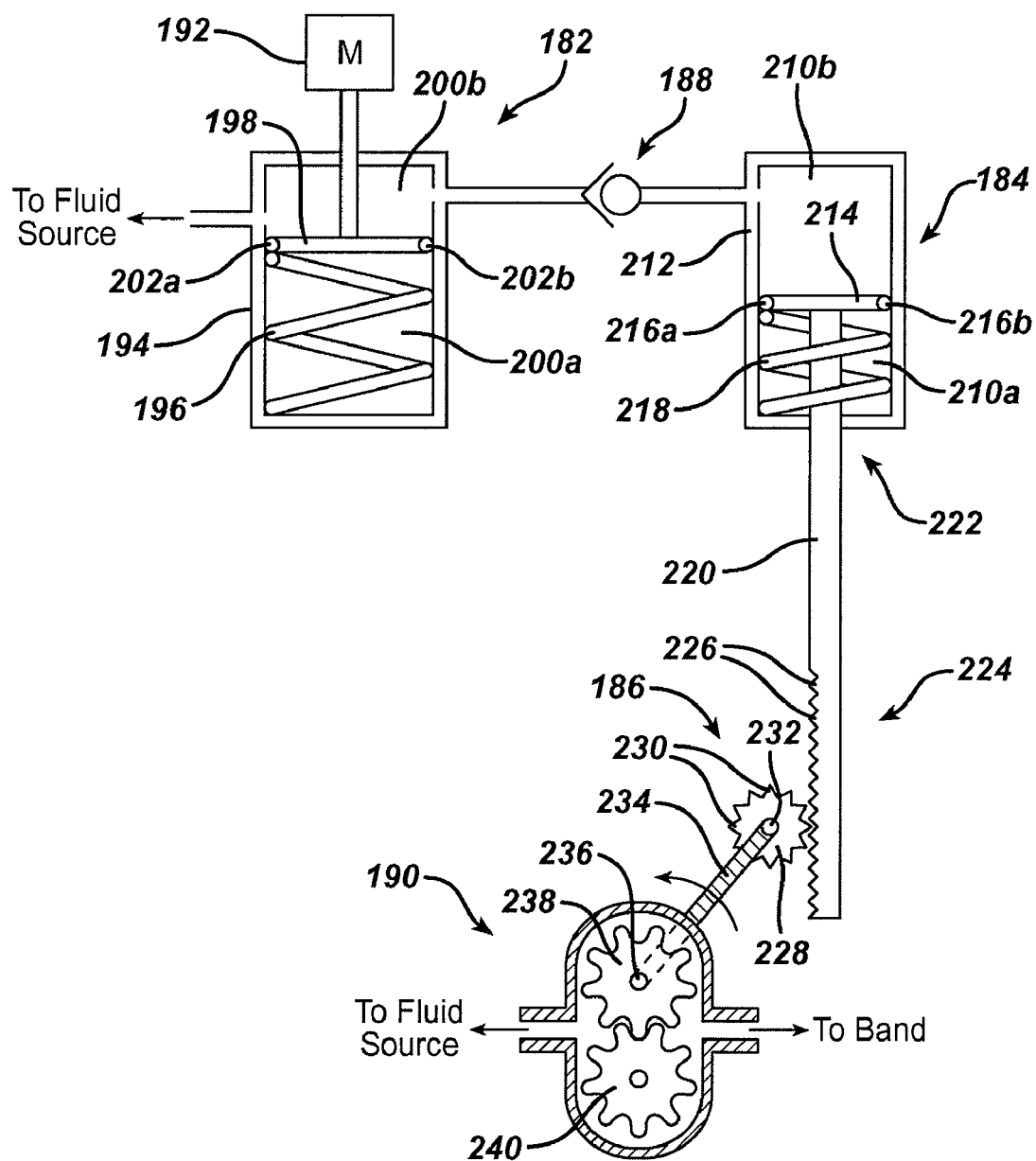
FIG. 6 is a schematic diagram of one exemplary configuration of the transient pressure control system of FIG. 5.

The energy charging mechanism 182 can receive energy in a variety of ways. For example, energy can be input to the energy charging mechanism 182 as applied kinetic energy, such as through motion of the patient in which the band 120 is implanted. Similar to a self-winding watch mechanism, as illustrated in the embodiment in FIG. 6, a mass 192 can oscillate in response to movement of the patient. Oscillation of the mass 192 can apply a force to an energy charging housing 194, e.g., to a biasing element such as a spring 196 disposed in the energy charging housing 194. The spring 196 can be any flexible elastic object having any shape. For example, the spring 196 can be a coil or helical spring having a cylindrical shape as shown in FIG. 6, although the spring 196 can have other shapes, such as conical or dual conical, and it can have individual coils of any shape, such as elliptical or rectangular. Other examples of the biasing element include an elastic band, thread, or cord, a bellows, a volute spring, and other similar types of flexible elastic objects. The spring 196 can also have a variety of sizes, and, if more than one spring is used, different springs used within the energy charging mechanism 182 can have different sizes and shapes. Furthermore, if more than one spring or other biasing element is used anywhere within the energy mechanism 180, each biasing element can be the same as or different from any other biasing element within the energy mechanism 180.

The mass 192 and the spring 196 can each be coupled to opposed sides of a spring coupling mechanism 198 disposed in the energy charging housing 194. The spring coupling mechanism 198 generally divides the energy charging housing 194 into two lower and upper cavities 200a, 200b having an inverse relationship, the lower cavity 200a including the spring 196 and the upper cavity 200b coupled to the mass 192 and the fluid source 170 and configured to contain fluid.

As the mass 192 moves (e.g., up and down, side to side, rotationally, etc.), a force can be applied to the spring coupling mechanism 198, which can move up and down within the energy charging housing 194, such as through the sliding of bearings 202a, 202b at the ends of the spring coupling mechanism 198 along the energy charging housing 194. ("Up" and "down" directions as discussed herein are relative to orientation of the elements involved. Depending on the orientation of the implanted elements and/or the position of the patient in which the elements are implanted, "up" and "down" can be different at different times and for different patients.) As the spring coupling mechanism 198 moves down, the spring 196 can be compressed within the energy charging housing 194, thereby decreasing the size of the lower cavity 200a while increasing the size of the upper cavity 200b. When enlarged, the upper cavity 200b can fill with fluid from the fluid source 170, which otherwise has a lower pressure than the upper cavity 200b. A valve 162 (see FIG. 5) can allow fluid to flow in the direction from the fluid source 170 to the energy charging mechanism 182.

The fluid source 170 can be a dedicated fluid source for the energy charging mechanism 182 and the energy storage mechanism 184 as explained below, e.g., the fluid source 170 need not be in fluid communication with the band 120. More choices of an implanted location of the energy mechanism 180 can be available if the fluid source 170 is so dedicated because the fluid source 170 need not be easily or at all accessible to any element included in the closed fluid circuit of the band 120. In some embodiments, upper fluid cavities 200b, 210b in the energy charging mechanism 182 and the energy storage mechanism 184, respectively, can contain any amount of a hydrogel, which can include any material, typically a biocompatible, water-insoluble, polymer material. With introduction of fluid into the upper fluid cavities 200b, 210b, the hydrogel can expand, thereby pushing down the respective spring coupling mechanisms 198, 214. The energy charging and energy storage mechanisms 182, 184 can, but need not, include the springs 196, 218, respectively, in their housings 194, 212 and coupled to the spring coupling mechanisms 198, 214 because the hydrogels can provide an adequate biasing force. When fluid flows out of the upper fluid cavities 200b, 210b, the hydrogel can shrink, thereby allowing the respective spring coupling mechanisms 198, 214 to move up.

The energy charging mechanism 182 can be configured to receive a finite amount of energy. For example, whether made from a rigid or a flexible material, the upper fluid cavity 200b of the energy charging housing 194 can have an internal area that can hold a finite amount of fluid. At some point during charging, the energy charging mechanism 182 may become fully charged. For example, the mass 192 may oscillate, but the spring 196 may be fully compressed (e.g., the spring coupling mechanism 198 cannot move any farther down inside the energy charging housing 194), thereby indicating that the energy charging mechanism 182 is fully charged. The amount of energy that can be applied to the energy charging mechanism 182 before it is fully charged can vary depending on any one or more factors, e.g., the size of the energy charging housing 194, the flexibility of the energy charging housing's composition material, the type of fluid in the upper cavity 200b, the size of the mass 192, the compressibility of the spring 196, the activity level of the patient, etc. It can take any amount of time to charge the energy charging mechanism 182 (e.g., fifteen minutes, one hour, two hours, five hours, twelve hours, twenty-four hours, etc.), although it preferably takes less than an amount of time in one day that the patient typically spends awake and mobile so as to allow for the possibility of the energy charging mechanism 182 to become fully charged during the day. The amount of energy and/or time needed to fully charge the energy charging mechanism 182 can vary from patient to patient and even for an individual patient as the patient loses weight or otherwise experiences changes that can affect the patient's treatment plan.

In another embodiment, energy can be input to the energy charging mechanism 182 from an external source (e.g., a magnet or other non-invasive charging device). The external source can be mobile (e.g., a wand or hand-held unit that can be waved or otherwise placed in proximity of the energy charging mechanism 182) or stationary (e.g., a bedside, desk or wall mounted, or car-mounted box that the patient can move near). Any user can so manually input energy (e.g., the patient in which the band 120 is implanted, a physician other medical personnel, etc.).

Figure 7:
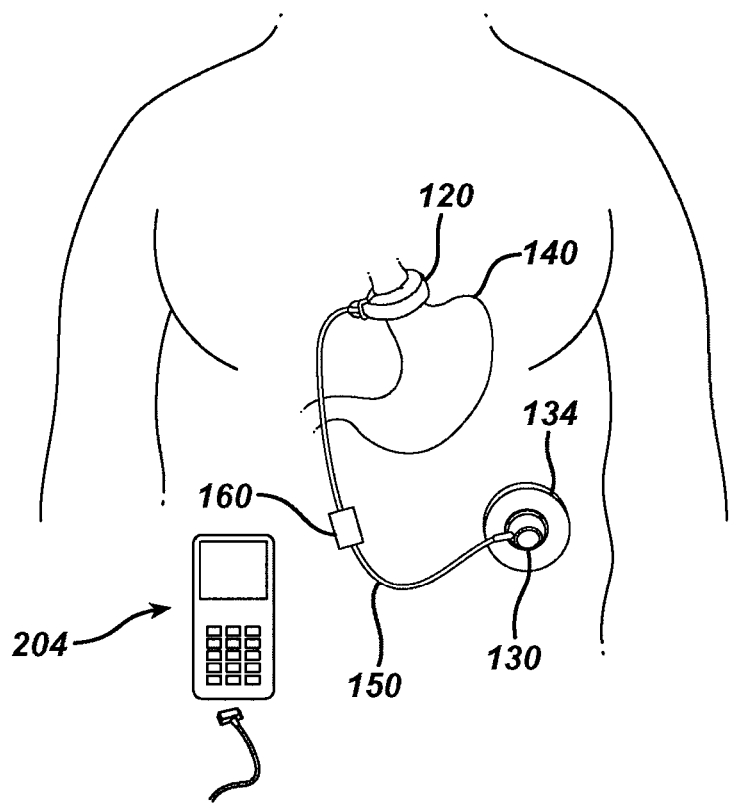
FIG. 7 is a schematic diagram of an external magnetic device for use with a food intake restriction system.

For example, as illustrated in FIG. 7, a magnetic device 204 can be placed in proximity to the energy charging mechanism 182, which is included in the control mechanism 160. The magnetic device 204 can be positioned on the skin surface above the energy charging mechanism 182 (which can be implanted beneath thick tissue, e.g., over 10 cm thick) to non-invasively apply energy to the energy charging mechanism 182. The magnetic device 204 can be an independent device or it can be electrically coupled (wirelessly or wired) to a control box that can display the status of the magnetic device's charging of the energy charging mechanism 182 and/or any other data. While shown in this example as located local to the patient, the control box 208 can be at a location local to or remote from the patient. When placed in proximity of the energy charging mechanism 182, the magnetic device 204 can apply a magnetic force to the energy charging mechanism 182 that can wind a magnetically driven spring, e.g., the spring 196. If the spring 196 is magnetically driven, the energy charging mechanism 182 need not include the mass 192.

Referring again to FIG. 6, the energy charging mechanism 182 can also transfer energy it receives to the energy storage mechanism 184. While various techniques can be used to transfer energy, in one embodiment the energy storage mechanism 184 can receive energy converted from kinetic energy derived from movement of the patient. To do so, the energy charging mechanism 182 and the energy storage mechanism 184 can be in fluid communication with each other. A valve 188, such as a check valve as shown, can allow fluid to flow in the direction from the energy charging mechanism 182 to the energy storage mechanism 184. When the mass 192 oscillates and the energy charging mechanism 182 charges, the energy charging mechanism 182 can release energy to the energy storage mechanism 184 by transferring fluid from the upper cavity 200b in the energy charging mechanism 182 into the upper cavity 210b in the energy storage mechanism 184. As another example, as the spring 196 magnetically winds, the energy charging mechanism 182 can transfer fluid to the energy storage mechanism 184.

The energy storage mechanism 184 can store energy in a variety of ways. Generally, the energy storage mechanism 184 can store potential energy, e.g., energy to be released to the energy release mechanism 186. For example, when the upper cavity 210b of the energy storage mechanism 184 receives fluid from the energy charging mechanism 182, the upper cavity 210b increases in size as it fills with fluid. Correspondingly, similar to the lower and upper cavities 200a, 200b in the energy charging mechanism 182, a lower cavity 210a included in a housing 212 of the energy storage mechanism 184 has an inverse relationship with the upper cavity 210b and decreases in size as the upper cavity 210b increases in size (and vice versa). Also similar to the energy charging mechanism 182, the energy storage mechanism 184 can include a spring coupling mechanism 214 movable within the housing 212 via opposed bearings 216a, 216b. Fluid pressure in the upper cavity 210b can push the spring coupling mechanism 214 down, thereby compressing a spring 218 disposed in the lower cavity 210a. As long as the energy charging mechanism 182 receives energy, the upper cavity 210b can fill with fluid and compress the spring 218. Once the energy storage mechanism 184 has stored the maximum amount of energy it can store, the spring 218 remains compressed as long as energy is being applied to the energy charging mechanism 182. With energy being input into the energy charging mechanism 182, a higher pressure can be maintained in the energy charging mechanism's upper cavity 200b than in the energy storage mechanism's upper cavity 210b that can, along with the valve 188 if present, prevent fluid from flowing from the energy storage mechanism 184 back into the energy charging mechanism 182.

Similar to the energy charging mechanism 182, the energy storage mechanism 184 can be configured to store a finite amount of energy. For example, whether made from a rigid or a flexible material, the upper cavity 210b of the energy storage mechanism 184 has an internal area that can hold a finite amount of fluid. The spring 218 when fully compressed indicates that the energy storage mechanism 184 is storing a maximum amount of energy. The maximum amount of stored energy can vary depending on any one or more factors, e.g., the size of the energy storage housing 212, the flexibility of the energy storage housing's composition material, the type of fluid in the upper cavity 210b, the compressibility of the spring 218, the size of a rack 220 at least partially disposed in the lower cavity 210a, etc. It can take also any amount of time to store energy in the energy storage mechanism 184 (e.g., fifteen minutes, one hour, two hours, five hours, twelve hours, twenty-four hours, etc.), although the amount of time is preferably less than an amount of time in one day that the patient typically spends awake and mobile so as to allow for the possibility of the energy storage mechanism 184 to store a maximum amount of energy during the day. Similarly, it can take any amount of time to release stored energy from the energy storage mechanism 184 to the energy release mechanism 186. The amount of energy and/or time needed to store a maximum amount of energy in the energy storage mechanism 184 can vary from patient to patient and even for an individual patient as the patient loses weight or otherwise experiences changes that can affect the patient's treatment plan.

Any mechanism can be used to transfer energy to the energy release mechanism 186, but in one embodiment, the rack 220 can be used. As mentioned above, the rack 220 can be at least partially disposed in the energy storage mechanism 184, e.g., in the lower cavity 210a including the spring 218. The rack 220 at its proximal portion 222 can be coupled to the spring coupling mechanism 214, and its distal portion 224 can be coupled to the energy release mechanism 186. The distal portion 224 of the rack 220 can have a plurality of teeth 226. The rack 220 can be coupled to the energy release mechanism 186 via a ratcheted escapement gear 228 that can engage the teeth 226. When the energy storage mechanism 184 stores energy (e.g., when fluid fills the upper cavity 210b and pushes down the spring coupling mechanism 214), the rack 220 can also be pushed down.

The rack 220 can have any configuration that allows for energy release from the energy storage mechanism 184. In the illustrated embodiment, the rack 220 linearly extends between the energy storage mechanism's spring coupling mechanism 214 and the escapement gear 228 as a substantially rectangular box-shaped structure, although the rack 220 can have any two-dimensional or three-dimensional shape and can have one or more non-linear portions. The rack 220 can also have any size, and it can be made of any type of material, but it is preferably made from a biocompatible material appropriate for use in a body. The teeth 226 formed on the rack 220 can also have any shape and size, and any number of teeth 226 can be oriented on the rack 220 to allow engagement with the escapement gear 228 and release of energy from the energy storage mechanism 184 when the rack 220 moves in the appropriate direction.

The energy release mechanism 186 can release stored energy from the energy storage mechanism 184 in a variety of ways. In the illustrated embodiment, energy is released by the escapement gear 228 turning in response to movement of the rack 220. The escapement gear 228 can have any shape and size and can be composed of any, typically biocompatible, material. The escapement gear 228 can include any number of gear teeth 230 that can engage the rack's teeth 226. The gear teeth 230 can also have any shape, size, and configuration on the escapement gear 228.

In an exemplary embodiment the escapement gear 228 is configured in a ratcheted configuration with the shaft 234 to rotate along with the shaft 234 in only one direction (counterclockwise in this embodiment) such that during energy storage, e.g., when the rack 220 is moving down, the escapement gear 228 does not rotate along with the shaft 234. The escapement gear 228 can rotate along with the shaft 234 when energy is released from the energy storage mechanism 184, e.g., when the rack 220 moves up and the rack's teeth 226 engage the gear's teeth 230. The escapement gear 228 is also configured to not rotate if the rack 220 is not moving, e.g., while the energy storage mechanism 184 is storing its maximum amount of energy but the energy charging mechanism 182 is still being charged. The coupling of the rack 220 to the spring coupling element 214 and/or the shapes of the teeth 226, 230 can prevent upward motion of the rack 220 (and hence turning of the escapement gear 228) while the energy charging mechanism 182 is being charged (e.g., when the spring coupling element 214 is being pushed or held down).

The energy storage mechanism 184 can release energy when it has any stored amount of energy and the energy charging mechanism 182 is not being charged. During energy release, fluid in the energy storage mechanism 184 can transfer out of the upper cavity 210b of the energy storage mechanism 184. Fluid can flow through a valve 206 (see FIG. 5) that allows fluid to flow in a single direction from the energy storage mechanism 184 to the fluid source 170. Alternatively, fluid can flow out of the energy storage mechanism 184 to the energy charging mechanism 182 if the valve 188 (and the valve 162) is a bi-directional valve that can switch to allow fluid to flow in one direction or in an opposite direction, in which case the valve 206 and its related connectors to the fluid source 170 and the energy storage mechanism 184 need not be present. As fluid flows out of the energy storage mechanism 184, the size of the energy storage mechanism's upper cavity 210b decreases, thereby increasing the size of the corresponding lower cavity 210a as the spring coupling mechanism 214 moves in an upward direction. The rack 220 coupled to the spring coupling mechanism 214 can also move up and engage and turn the escapement gear 228. The escapement gear 228 can be coupled to a proximal end 232 of a drive shaft 234, which can be coupled at its distal end 236 to the pump 190. The drive shaft 234 can have any size, shape, and configuration that allows for its coupling with the energy storage mechanism 184 and the pump 190. In the illustrated embodiment, the drive shaft 234 linearly extends between with the energy storage mechanism 184 and the pump 190 as a substantially cylindrical rod, although drive shaft 234 can have any two-dimensional or three-dimensional shape and can be non-linear. The drive shaft 234 can be made of any type of material.

As the escapement gear 228 turns, the drive shaft 234 can also rotate about a longitudinal axis of the drive shaft 234, thereby driving the pump 190 to pump fluid from the fluid source 170 into the band 120. The energy stored in the energy storage mechanism 184 can continue to drive the pump 190 through the stored energy's release until all stored energy is released or until the energy charging mechanism 182 starts charging again. The amount of time it takes to release energy stored in the energy storage mechanism 184 can vary (e.g., fifteen minutes, one hour, two hours, five hours, twelve hours, twenty-four hours, etc.). The maximum amount of time for energy release generally corresponds to continuous, uninterrupted release of the maximum amount of energy that can be stored in the energy storage mechanism 184 and to an amount of time the energy charging mechanism 182 spent releasing that maximum amount of energy to the energy storage mechanism 184. In this way, the pump 190 can pump fluid to the band 120 for a time, e.g., one hour, after the patient ceases activity, e.g., at the end of a day. In this way, after the pump 190 ceases pumping fluid to the band 120, the band 120 can release fluid, thereby allowing restriction formed by the band 120 to decrease during periods of patient inactivity, e.g., at night. The band's pressure can at least remain constant if the band does not release or ceases releasing fluid, e.g., because a pressure of fluid in the band 120 is less than that of fluid in the fluid source 170, because no fluid remains in the band 120, etc. Correspondingly, when the patient resumes activity, e.g., at the beginning of the day, pressure in the band 120 will not increase and the band's pressure can remain at a low level for a certain amount of time defined by the amount of time the energy charging mechanism 182 is charged before the energy storage mechanism 184 begins releasing stored energy to drive the pump 190.

The pump 190 can have any configuration that allows fluid communication between the fluid source 170 and the band 120, such as a positive displacement pump (e.g., a screw pump, a gear pump, etc.) or a centrifugal pump (e.g., a scroll pump, etc.). For example, as illustrated in FIG. 6, the pump 190 can be a gear pump having a drive gear 238 and an idle gear 240. The drive and idle gears 238, 240 can each have any shape and size and be composed of any, typically biocompatible, material. The drive and idle gears 238, 240 can each include any number of teeth that can engage with one another such that when the drive gear 238 is driven to turn by rotation of the drive shaft 234 (the distal end 236 of which can be coupled to the drive gear 238), the idle gear 240 also turns. The teeth of the drive and idle gears 238, 240 can also have any shape, size, and configuration on their respective drive and idle gears 238, 240. The pump 190 can couple to each of the fluid source 170 and the band 102 via catheters (e.g., the catheter 150) or any other connectors. As mentioned above, the fluid source 170 may not be the same fluid source used for the energy charging mechanism 182 and the energy storage mechanism 184.

Rotation of the drive and idle gears 238, 240 (in this embodiment, in a counter-clockwise direction) can pump fluid away from the fluid source 170 and into the band 120, thereby increasing an amount of restriction applied to the stomach 140 by the band 120. When the energy release mechanism 186 is not releasing energy to the pump 190, the pump 190 can allow fluid to be released from the band 120 and into the fluid source 170. Alternatively, in some embodiments, one or more valves 208 (see FIG. 5) can be disposed between the fluid source 170 and the pump 190 that allows fluid to flow in a single direction from the fluid source 170 the band 120. In this way, when the pump 190 ceases running (e.g., when all energy is released from the energy storage mechanism 184 and the drive shaft 234 stops turning the drive gear 238), pressure can be maintained in the band 120. The one or more valves 208 can be configured to have a pre-set maximum pressure level and open when pressure in the band 120 is greater than the pre-set maximum pressure level, as discussed further below. The one or more valves 208 can also be configured to be manually locked and unlocked, also as described further below.

Figure 8:
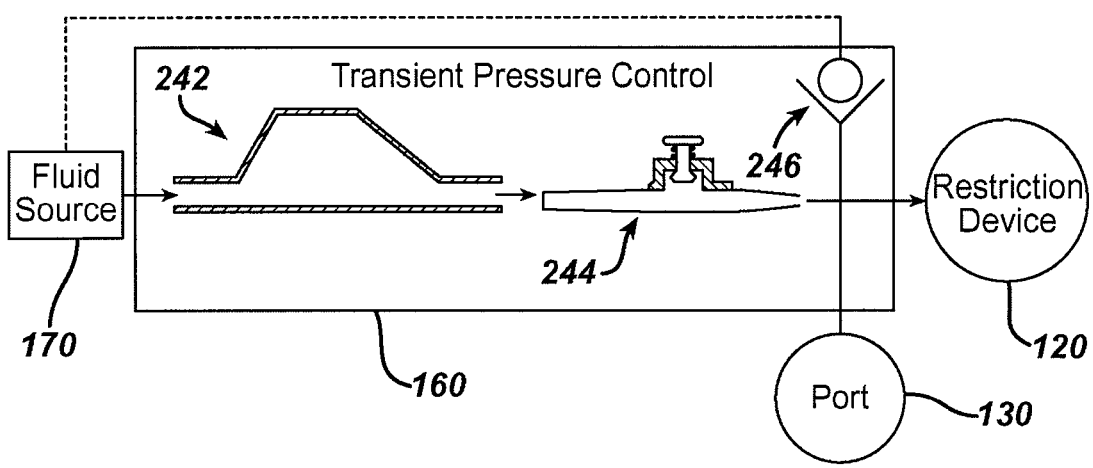
FIG. 8 is a schematic diagram of another exemplary embodiment of a food intake restriction system having a transient pressure control system with a subcutaneous pump.

In other embodiments, the control mechanism 160 can include a subcutaneous pumping system, such as in the embodiment illustrated in FIG. 8. The control mechanism 160 can include a subcutaneous pumping mechanism, such as a subcutaneous flexible pump 242, a first valve 244, and a second valve 246. One or more additional valves can be included in the system 100, such as between the fluid source 170 and the flexible pump 242 (allowing fluid to flow in a direction from the fluid source 170 to the flexible pump 242) and between the flexible pump 242 and the first valve 244 (allowing fluid to flow in a direction from the flexible pump 242 to the band 120). Generally, the flexible pump 242 can be manually activated to release fluid from the fluid source 170 into the band 120. The first valve 244 can be coupled between the flexible pump 242 and the band 120 to allow the flexible pump 242 to pump fluid in a single direction toward the band 120. The second valve 246 can be coupled with the band 120, and optionally with the fluid source 170, to allow fluid to flow in a single direction out of the band 120 when a pressure of fluid in the band 120 is greater than a pre-set pressure limit. Fluid can flow out of the second valve 246 to the fluid source 170 (in which case the fluid source 170, the control mechanism 160, the port 130 (if present and separate from the fluid source 170), and the band 120 can form a closed fluid circuit) or to a location in the body. In this way, pressure of fluid in the band 120 can be increased by pumping the flexible pump 242 and allowing fluid to flow into the band 120, but the second valve 246 can prevent a pressure of fluid in the band 120 from exceeding a maximum limit. The second valve 246 can also be coupled to the port 130 such that, if fluid added to the system 100 through the port 130 increases a pressure of fluid in the band 120 beyond the pre-set pressure limit, the second valve 246 can open to allow fluid to flow out of the band 120.

The flexible pump 242 can have a variety of configurations, shapes, and sizes. For example, the flexible pump 242 can include a silicone bulb, although the flexible pump 242 can be made of any type of material, typically a biocompatible material appropriate for use in a body. An exemplary flexible pump 242 is disclosed in more detail in commonly-owned U.S. Publication No. 2005/0272968 entitled "Implantable Adjustable Sphincter System," filed on Jun. 2, 2004 which is hereby incorporated by reference in its entirety. In general, the flexible pump 242 can be implanted beneath tissue and manually activated through tissue, such as by manually applying pressure on the patient's skin above the site where the flexible pump 242 is located. Alternatively, the flexible pump 242 can be palpated from within the patient by the flexing of abdominal muscles or other bodily motion. Preferably, the flexible pump 242 is sized to pump an appropriate amount of fluid while not being too obtrusive to the patient.

The flexible pump 242 can be implanted at any subcutaneous location, such as in the abdominal cavity. In this way, the flexible pump 242 can be activated from within a patient through percutaneous palpation through relatively thick abdominal skin from one side only. The flexible pump 242 can be placed against fascia that resists inward pressure to allow pumping by applying pressure on the side of the flexible pump 242 opposite to the fascia. For example, the patient in which the flexible pump 242 is implanted can perform a prescribed motion (e.g., bending over, flexing of muscle, one or more sit-ups, etc.), the action of which can internally depress the flexible pump 242.

The first and second valves 244, 246 can also have a variety of configurations, shapes, and sizes. Examples of the first and second valves 244, 246 include check valves and release valves known to those skilled in the art. Exemplary valves are disclosed in more detail in commonly-owned U.S. Publication No. 2005/0272968 (previously mentioned) and in U.S. application Ser. No. 11/965,334 filed on the same day herewith entitled "Fluid Logic for Regulating Restriction Devices," which is hereby incorporated by reference in its entirety. For example, the second valve 246 can be pre-set (fixedly or adjustably) to open at a pre-set pressure, thereby allowing a maximum pressure in the system to be set. A minimum pressure in the system can be defined by an amount of fluid available to be transferred into the band 120 (e.g., by an amount of fluid in the fluid source 170 and elsewhere in the close fluid circuit including the band 120), and together the minimum and maximum pressures can define a pressure range controllable as desired to control pressure with that range.

Figure 9:
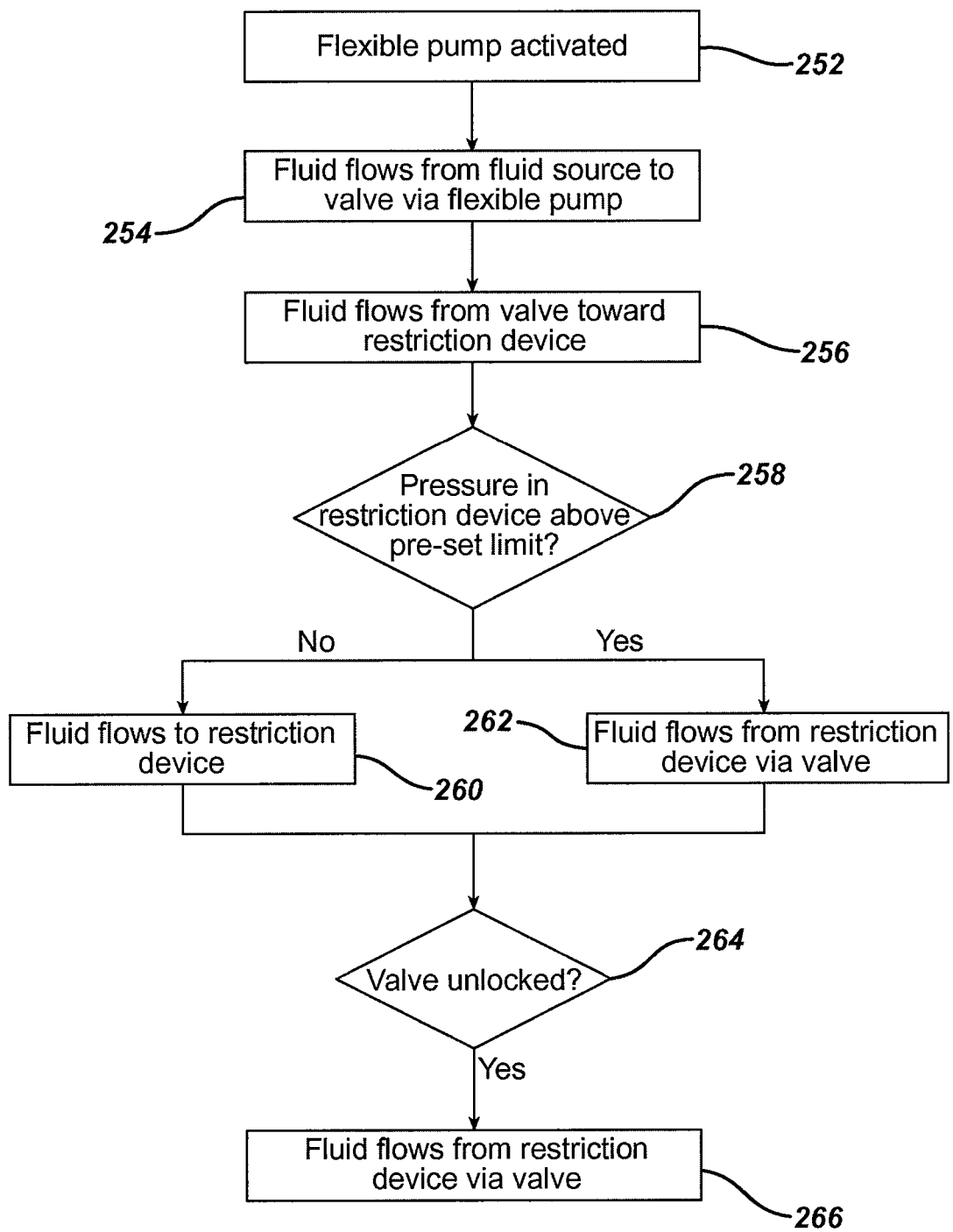
FIG. 9 is a flow diagram showing one embodiment of a transient pressure control protocol for the food intake restriction system of FIG. 8.

As illustrated in one embodiment of a process shown in FIG. 9, the control mechanism 160 including the flexible pump 242 and the valves 244, 246 can generally control pressure in the band 120. While the process shown in FIG. 9 is discussed with relation to the elements included in FIGS. 1A-4, and 8 (and FIG. 10, below), a person skilled in the art will appreciate that the process can be modified to include more or fewer elements in various configurations, and it can be performed in the system 100 or in another similar system having other similar elements.

In use, the flexible pump 242 can be activated 252 to cause fluid to flow 254 from the fluid source 170 into the flexible pump 242 and from the flexible pump 242 through 254 the first valve 244 and into 256 the band 120. The flexible pump 242 can be activated 252 in a variety of ways, such as by manually, percutaneously palpating the flexible pump 242 as mentioned above. The pressure created by the flexible pump 242 will eventually exceed the pressure at which the first valve 244 opens, causing fluid to flow from the fluid source 170, through the first valve 244, and into the band 120. As discussed above, a valve (e.g., a check valve) can be coupled between the fluid source 170 and the flexible pump 242 that allows fluid to flow in a direction from the fluid source 170 to the flexible pump 242 while preventing fluid from flowing from the flexible pump 242 to the fluid source 170. Fluid flow from the fluid source 170 through the flexible pump 242 and into the band 120 will increase the pressure in the band 120 and thus decrease the size of the stoma in the stomach 140.

While the flexible pump 242 is described as being manually operable to transfer fluid between the fluid source 170 and the band 120, the flexible pump 242 need not actually transfer fluid from the fluid source 170 into the band 120. In other words, the pressure in the band 120 can be increased by the mere shifting of fluid from the fluid source 170 toward the band 120 (e.g., by pumping fluid from the fluid source 170 to the flexible pump 170, which displaces fluid previously in the flexible pump 170 into the band 120), as such shifting will cause similar shifting of fluid "upstream" of the fluid source 170. It is not necessary for fluid being introduced into the band 120 by palpation of the flexible pump 242 to have actually come from the fluid source 170. This additional fluid can originate from any part of the system 100 between the band 120 and the fluid source 170. Furthermore, as discussed above, the fluid source 170 can have various configurations, and the system 100 can include any number of fluid sources.

The flexible pump 242 can be activated 252 any number of times and at any frequency. For example, the system 100 can be implanted in a patient with the fluid source 170 at least partially full. Subsequent to implantation, the band 120 can be filled with fluid, such as by activating 252 the flexible pump 242 and/or by a physician (or other medical personnel) using a needle and syringe to introduce fluid through the port 130. The patient's treatment plan can include a prescribed or recommended number of flexible pump activations (e.g., daily, hourly, weekly, monthly, etc.) and any number of depressions per activation (e.g., one, two, etc.). The number of prescribed or recommended number of flexible pump activations can vary from patient to patient and even for an individual patient as the patient loses weight or otherwise experiences changes that can affect the patient's treatment plan. Having such a pumping schedule or regimen can help accommodate any pressure losses that can occur in the band 120 as the patient loses weight. However, if the patient neglects to activate 252 the flexible pump 242 as prescribed, recommended, or otherwise desired, the system 100 can retain functionality with pressure in the band 120 generally following an exponential pressure decrease (e.g., a sequence 250 in FIG. 11 discussed below).

As indicated above, the system can also include a second valve 246, or other release mechanism, that releases fluid from the band 120 if the pressure in the band 120 exceeds a maximum threshold pressure. The second valve 246 generally has two positions, a closed position preventing fluid flow therethrough and an open position allowing fluid to flow in a single direction therethrough (e.g., out of the band 120). The second valve's default position is closed such that any fluid flowing toward the band 120 flows into the band 120 and not into the second valve 246. The second valve 246 can, however, determine 258 if pressure of fluid in the band 120 is greater than a pre-set pressure limit. If not, the second valve 246 stays in the closed position (or moves to the closed position from the open position) to allow 260 fluid to flow into the band 120. If the pre-set pressure limit is exceeded, then the second valve 246 can move to the open position to allow 262 fluid to flow out of the band 120.

The second valve 246 can control fluid flow in a variety of ways. Examples of systems that the second valve 246 can use to so control fluid flow are disclosed in more detail in the aforementioned U.S. Publication No. 2005/0272968 and the aforementioned U.S. application Ser. No. 11/965.334 filed on the same day herewith entitled "Fluid Logic for Regulating Restriction Devices". The second valve 246 can have virtually any configuration that is effective to control fluid flow, but in certain exemplary embodiments the second valve 246 has a pre-set pressure limit, or a pre-set pressure range, that the second valve 246 relies on to achieve a desired pressure in the band 120. The second valve 246 can thus control an amount of fluid added into and/or removed from the band 120, thereby controlling an amount of restriction that is formed by the band 120.

The second valve 246 can have a maximum pre-set pressure limit such that, when the pressure of the fluid in the band 120 exceeds the maximum pre-set pressure limit (due to a food blockage in the pathway, too many palpations of the flexible pump 242, etc.), fluid is released from the band 120 (into the fluid source 170 (if the second valve 246 is coupled to the fluid source) or to another fluid release location in the body) to thereby decrease the pressure in the band 120 (thereby decreasing the amount of restriction) until the pressure is equal to or less than the maximum pre-set pressure limit. Having a pre-set pressure limit is particularly advantageous as it allows for small variations in the pressure in the band 120, for example while the patient is eating, without continuously altering the fluid pressure in the band 120, yet it is effective to maintain the pressure within a desired range to provide an amount of restriction necessary for the band 120 to be effective.

The first valve 244 can also be configured to have locked and unlocked positions. The locked and unlocked positions generally correspond, respectively, to the closed and open positions discussed above for the second valve 246 such that fluid can flow 266 through the first valve 244 in the unlocked position 264 but not in the locked position. While the second valve 246 switching between the closed and open positions can be substantially automatic, the first valve 244 can, in some embodiments, be configured to be manually released from the locked position to the unlocked position and vice versa.

The first valve 244 can be manually switched between the locked and unlocked positions in a variety of ways. Examples of the first valve 244 that can switch between locked and unlocked positions are disclosed in more detail in the aforementioned U.S. Publication No. 2005/0272968. Generally, the first valve 2464 can be prevented from manually switching between the locked and unlocked positions without authorization from a physician (or other medical personnel), whether the patient or the another person performs the manual switching, such as in an emergency or otherwise abnormal situation when the first valve 244 should be unlocked because fluid should be released from the band 120 due to, e.g., a fold in the band 120, patient discomfort, malfunction of the pre-set pressure limit logic of the second valve 246, etc.

For example, the first valve 244 can include a mechanical locking element to allow manual switching of the first valve 244 between the locked and unlocked positions. One embodiment of a mechanical locking element for the first valve 244 includes a mechanism responsive to manual palpation. By way of example only, the first valve 244 can be constructed such that the configuration of the first valve 244 can be switched between the locked and unlocked positions by percutaneous manipulation of a switch, lever, dial, button, or any other suitable switching alternative or combination thereof. Where the first valve 244 configuration is manually switchable by such a mechanism or mechanisms, the first valve 244 can give tactile feedback indicating the configuration of the first valve 244 based on the position of the switching mechanism or mechanisms. Furthermore, a series of one or more percutaneous manipulations can be required to switch the first valve 244 between the locked and unlocked positions, e.g., depressions of mechanical elements in a specific order. The patient can be required to contact a physician (or other authorized medical personnel) to receive the correct series of percutaneous manipulations, thereby allowing the physician to be aware of and/or authorize the fluid adjustment.

Another embodiment of a mechanical locking element for the first valve 244 includes a mechanism responsive to a magnetic field. By way of example only, the first valve 244 can include an array of magnets. When a particular magnetic "key" is placed in proximity of the first valve 244, the first valve 244 can be switched between the locked and unlocked positions. The "key" can be secret and only provided or revealed to the patient by a physician (or other authorized medical personnel).

Another example of how the first valve 244 can be manually switched between the locked and unlocked positions includes transcutaneous transmission of non-electromagnetic energy to the first valve 244. By way of example only, the first valve 244 can be constructed such that the first valve 244 can be switched between locked and unlocked positions by way of ultrasound. In other words, the first valve 244 can be made responsive to ultrasound such that the first valve 244 can be actuated or otherwise placed in various configuration(s) by mechanical resonance and/or other effects created by ultrasound.

The first valve 244 can be made to respond differently to different frequencies of ultrasound. For example, a first frequency can actuate a first valve in the first valve 244 or otherwise place the first valve 244 in the unlocked position such that fluid is permitted to flow out of the band 120, while fluid is prevented from flowing from the fluid source 170 toward the band 120. A second frequency can actuate a second valve in the first valve 244 or otherwise place the first valve 244 in the locked position, such that fluid is prevented from flowing into the band 120 through the first valve 244. The first valve 244 can be constructed such that the first valve 244 is in the locked position by default (e.g., when it is not being exposed to the first frequency of ultrasound). In such an embodiment, the response of the first valve 244 to the first frequency may be substantially temporally limited to the duration of the exposure of the first valve 244 to the first frequency. In other words, the first valve 244 can be constructed such that the first valve 244 would be placed in the unlocked position only for the approximate time of its exposure to the first frequency.

Alternatively, the adjustment can be enabled by a wide range of ultrasonic frequencies, relying upon sufficient strength of ultrasonic energy to avoid inadvertent enablement. Even given brief exposure to ultrasonic energy, such as for a medical diagnostic procedure wherein adjustment is not intended, integrating primary value control with pumping may ensure maintenance of fluid pressure. The ultrasonic energy can assist in overcoming static friction, for instance, within dynamic seals of the flexible pump 242 that enable pumping to occur, which would otherwise resist movement.

In such an ultrasonically enabled first valve 244, direction of adjustment can be controlled by having the flexible pump 242 comprised of two parallel pumps (e.g., check valves), each parallel pump controlled to allow fluid in opposite directions with each opposing all flow when in an unactuated state. The second valve 246 can be similarly constructed. Thus, the ultrasonic enablement avoids inadvertent actuation of the flexible pump 242, yet specifically tailored ultrasonic sources need not be used.

Figure 10:
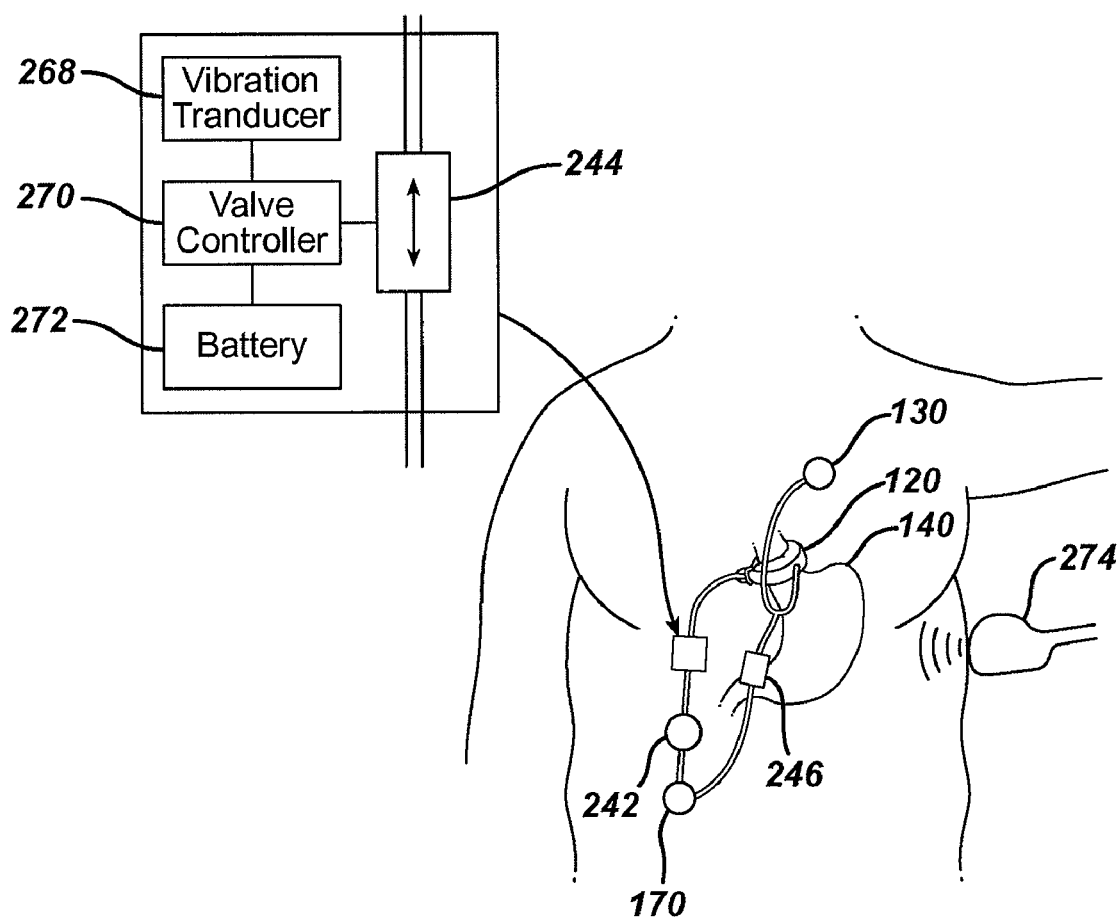
FIG. 10 is a schematic diagram of an ultrasonically activated valve assembly for use with the food intake restriction system of FIG. 8.

As another example, shown in FIG. 10, an electrically-powered valve controller 270 can be energized or activated by an ultrasonic frequency coming from an ultrasound emitter 274, such as with a vibration transducer 268, and electromechanically actuate a valve or valves in response thereto, or otherwise change configurations of the first valve 244 in response to an ultrasonic frequency. In this embodiment, the first valve 244 can be coupled with or include such a transducer 268 and a valve controller 270, along with a battery 272 as a source of power to the valve or valves. As merely providing power to a valve or valves, such a battery 272 can have a longer life than a battery that supplies power to a pump, such as those found in conventional TET-operated implant systems. Additionally, the first valve 244, including the transducer 268, the controller 270, and the battery 272, can all be electrically shielded to avoid EMIC considerations that are typically appurtenant to conventional TET systems.

As to any embodiment where the first valve 244 is responsive to ultrasound, it may be desirable to limit the responsiveness of the first valve 244 to certain patterns of ultrasound. That is, rather than being immediately responsive to a certain frequency or frequencies of ultrasound, the first valve 244 could be made such that the first valve 244 will only respond to a frequency or frequencies of ultrasound being emitted in a certain pattern or patterns. By way of example only, such pattern-based requirements can alleviate concerns that the first valve 244 may respond to ultrasound being emitted by unforeseen sources of ultrasound.

However configured to be manually switched between the locked and unlocked positions, the first valve 244 (and/or controls for manually switching the first valve 244 between the locked and unlocked positions) can be located on a region of a patient's anatomy that is difficult for the patient to access without assistance, e.g., on the patient's back. In this way, the patient can be prevented from manually releasing fluid from the band 120, and hence from decreasing a pressure of the band 120, without assistance and/or appropriate medical authorization.

Figure 11:
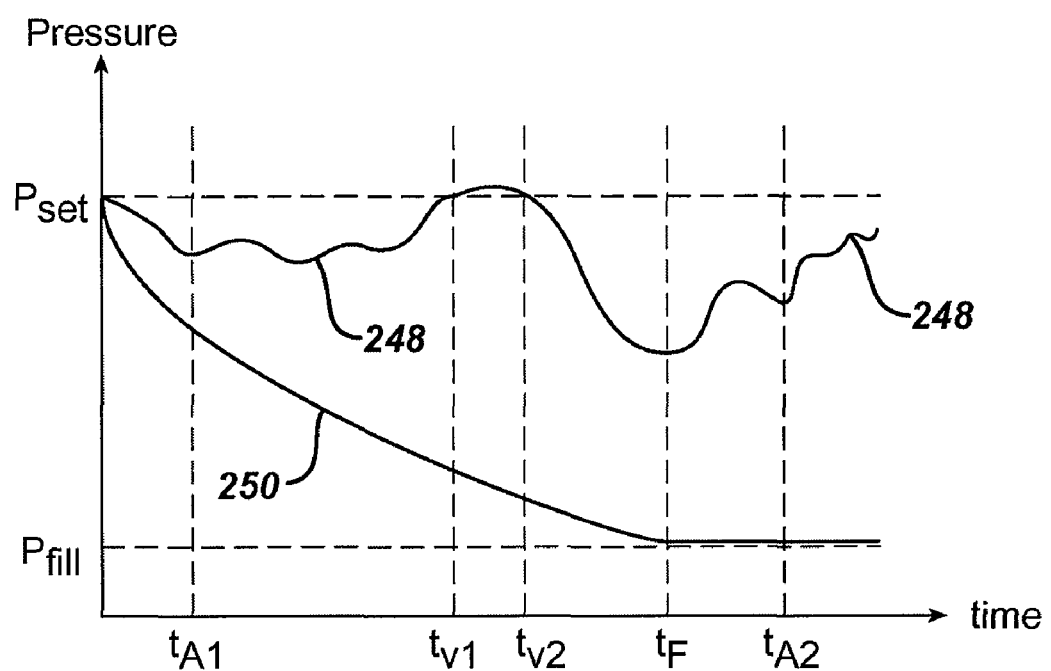
FIG. 11 is a graphical representation showing sample pressure measurements in the food intake restriction system of FIG. 8.

As a non-limiting example, FIG. 11 shows an example sequence 248 of pressure measurements in the band 120 over time. The pressure values and times shown in FIG. 11 are examples only; the pressure values can include any values or ranges of values over any period of time. A person skilled in the art will appreciate that the pressure measurements can include sensed data values gathered by a sensing device (e.g., the pressure reading device 134). Furthermore, a pressure setpoint $P_{set}$ (generally, a desired maximum amount of pressure in the band 120) and a pressure fillpoint $P_{fill}$ (generally, a minimum amount of pressure in the band 120 at which a fill of fluid into the system 100 including the band 120 is desirable or required) can one or both change over time, e.g., as the patient gains or loses weight. Another example sequence 250 of pressure measurements is shown in FIG. 11 that corresponds to an exponential decrease in pressure from $P_{set}$ to $P_{fill}$, indicating a constant pressure profile, e.g., a possible pressure profile if the flexible pump 242 is not pumped to increase an amount of fluid in the band 120 between a zero time and a time $t_F$ when the pressure in the sequence 250 approaches $P_{fill}$. Although the plot of FIG. 11 is discussed with relation to the elements included in FIG. 8, a person skilled in the art will also appreciate that this or a similar plot can be obtained using this or a similar control mechanism 160.

As shown in the pressure sequence 248, the pressure in the band 120 at a zero time begins at $P_{set}$ and decreases over time. The pressure in the band 120 can decrease due to one or more factors, such as a change in patient anatomy (e.g., due to weight loss), eating, upon opening (automatic or manual) of the first valve 244 and/or the second valve 246, upon a band malfunction, etc. When the pump 242 is activated, such as at times $t_{A1}$ and $t_{A2}$, the pressure increases as fluid flows into the band 120. Pressure in the band 120 can also increase due to other factors, such as a change in patient anatomy (e.g., due to weight gain), eating, introduction of fluid to the system 100, upon a band malfunction, etc. If pressure in the band 120 increases to $P_{set}$, such as at a time $t_{V1}$, the band pressure has reached a pre-set pressure limit, and the second valve 246 can open and allow fluid to flow out of the band 120. The second valve 246 can remain open until pressure in the band 120 decreases to $P_{set}$ at a time $t_{V2}$, at which time the second valve 246 can close.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK® (available from DuPont of Wilmington, Del.) bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of forming a restriction in a patient, comprising:
applying energy to an energy charging mechanism;
delivering the energy to an energy storage mechanism which stores the energy; and
releasing the stored energy from the energy storage mechanism to cause fluid to flow from a fluid source into a restriction device that is implanted to form a restriction in a pathway;
wherein the energy is mechanically applied without using electrical power, the energy is mechanically delivered without using electrical power, and the stored energy is mechanically released without using electrical power;
and wherein applying the energy comprises transferring a second fluid from a second fluid source to the energy charging mechanism, the fluid source not being in fluid communication with the second fluid source.

2. The method of claim 1, wherein fluid flow from the fluid source into the restriction device increases an amount of restriction applied to the pathway by the restriction device.

3. The method of claim 1, wherein applying energy comprises applying kinetic energy generated by movement of a patient having the restriction device implanted therein.

4. The method of claim 1, wherein applying energy comprises placing a magnetic device in proximity to the energy charging mechanism.

5. The method of claim 1, wherein energy stored in the energy storage mechanism is released only when the energy charging mechanism is not delivering energy to the energy storage mechanism.

6. The method of claim 1, wherein the energy storage mechanism releases energy to an energy release mechanism that causes a pumping mechanism to pump fluid from the fluid source into the restriction device.

7. The method of claim 1, wherein a pump pumps fluid in a single direction from the fluid source toward the restriction device.

8. The method of claim 1, wherein, when a pressure of fluid in the restriction device is greater than a pre-set pressure limit of a valve coupled to the restriction device, the valve opens to allow fluid to flow out of the restriction device.

9. The method of claim 8, wherein fluid flows out of the restriction device toward the fluid source when a second valve coupled to the restriction device is manually released from a locked position.

10. The method of claim 1, further comprising adjusting a pre-set pressure limit.

11. The method of claim 1, wherein delivering the energy comprises transferring fluid from the energy charging mechanism to the energy storage mechanism, the energy charging mechanism and the energy storage mechanism forming a closed fluid circuit such that the fluid that flows from the fluid source into the restriction device is not included in the closed fluid circuit.

12. The method of claim 1, wherein delivering the energy comprises transferring the second fluid from the energy charging mechanism to the energy storage mechanism.

13. The method of claim 1, wherein releasing the stored energy causes a gear to rotate to pump the fluid from the fluid source into the restriction device.

14. The method of claim 1, wherein the fluid source is not in fluid communication with the energy storage mechanism and the energy charging mechanism such that the fluid in the fluid source that can flow into the restriction device cannot flow into the energy storage mechanism or the energy charging mechanism, and the fluid that can transfer from the energy storage mechanism into the energy charging mechanism and that can transfer from the energy charging mechanism into the energy storage mechanism cannot flow into the restriction device.

15. A method of forming a restriction in a patient, comprising:

applying energy to an energy charging mechanism;

delivering the energy to an energy storage mechanism which stores the energy; and releasing the stored energy from the energy storage mechanism to cause fluid to flow from a fluid source into a restriction device that is implanted to form a restriction in a pathway;

wherein the energy is mechanically applied without using electrical power, the energy is mechanically delivered without using electrical power, and the stored energy is mechanically released without using electrical power;

wherein, when energy is applied to the energy charging mechanism, fluid is transferred from the energy charging mechanism into the energy storage mechanism to deliver the energy to the energy storage mechanism;

wherein releasing the stored energy comprises transferring fluid from the energy storage mechanism into the energy charging mechanism to cause the fluid to flow from the fluid source into the restriction device; and wherein the fluid source is in fluid communication with the energy storage mechanism and the energy charging mechanism such that the fluid in the fluid source that can flow into the restriction device can flow into the energy storage mechanism and the energy charging mechanism.

16. The method of claim 15, wherein, when the energy storage mechanism releases the stored energy, fluid is transferred from the energy storage mechanism to the fluid source.

* * * * *